US007414146B2

(12) United States Patent
Slusarek et al.

(10) Patent No.: US 7,414,146 B2

(45) **Date of Patent: *Aug. 19, 2008**

(54) IMAGING ELEMENT CONTAINING A BLOCKED PHOTOGRAPHICALLY USEFUL COMPOUND

(75) Inventors: Wojciech K. Slusarek, Rochester, NY (US); Xiqiang Yang, Webster, NY (US); David H. Levy, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 850 days.

This patent is subject to a terminal disclaimer.

(21) Appl. No.: 09/904,616

(22) Filed: Jul. 13, 2001

(65) Prior Publication Data

US 2002/0019571 A1 Feb. 14, 2002

Related U.S. Application Data

(62) Division of application No. 09/711,769, filed on Nov. 13, 2000, now Pat. No. 6,319,640.

(51) Int. Cl.
*C07C 261/00* (2006.01)

(52) U.S. Cl. ........................................................ 560/33

(58) Field of Classification Search ................. 564/154, 564/162, 214

See application file for complete search history.

(56) References Cited

U.S. PATENT DOCUMENTS

| | | | |
|---|---|---|---|
| 3,342,599 A | 9/1967 | Reeves | |
| 4,060,418 A | 11/1977 | Waxman et al. | |
| 4,157,915 A | 6/1979 | Hamaoka et al. | |
| 5,019,492 A | 5/1991 | Buchanan et al. | |
| 6,242,166 B1 * | 6/2001 | Irving et al. | |
| 6,319,640 B1 * | 11/2001 | Slusarek et al. | ............... 430/21 |

FOREIGN PATENT DOCUMENTS

EP 0 393 523 A2 10/1990

OTHER PUBLICATIONS

Research Disclosure No. 12924, vol. 129, 1975, pp. 27-30, Kenneth Mason Publications, Ltd., Dudley Annex, 12a North Street, Emsworth, Hampshire P010 7DQ, England.

Patent Abstracts of Japan, vol. 007, No. 196, (P-219), Aug. 26, 1983 & JP 58 095344 A (Konishiroku Shashin Kogyo KK), Jun. 6, 1983, p. 293.

* cited by examiner

*Primary Examiner*—Samuel A Barts

(57) ABSTRACT

This invention relates to an imaging element comprising an imaging layer having associated therewith a compound of Structure I:

FIG. 1

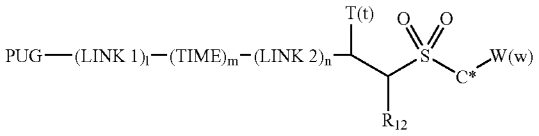

In the above Structure I, the substituents are as defined in the application. Such compounds have good reactivity and can by used to block photographically useful compounds such as developing agents until thermally activated under preselected conditions. Compounds according to the present invention are especially useful in color photothermographic imaging elements.

6 Claims, 2 Drawing Sheets

IMAGING ELEMENT CONTAINING A BLOCKED PHOTOGRAPHICALLY USEFUL COMPOUND

CROSS REFERENCE TO RELATED APPLICATIONS

This is a Divisional of application Ser No. 09/711,769, filed Nov. 13, 2000 now U.S. Pat. No. 6,319,640.

FIELD OF THE INVENTION

This invention relates to an imaging element containing a blocked photographically useful compound such as a developing agent.

BACKGROUND OF THE INVENTION

In conventional color photography, films containing light-sensitive silver halide are employed in hand-held cameras. Upon exposure, the film carries a latent image that is only revealed after suitable processing. These elements have historically been processed by treating the camera-exposed film with at least a developing solution having a developing agent that acts to form an image in cooperation with components in the film. Developing agents commonly used are reducing agents, for example, p-aminophenols or p-phenylenediamines.

Typically, developing agents (also herein referred to as developers) present in developer solutions are brought into reactive association with exposed photographic film elements at the time of processing. Segregation of the developer and the film element has been necessary because the incorporation of developers directly into sensitized photographic elements can lead to desensitization of the silver halide emulsion and undesirable fog. Considerable effort, however, has been directed to producing effective blocked developing agents (also referred to herein as blocked developers) that might be introduced into silver halide emulsion elements without deleterious desensitization or fog effects. Accordingly, blocked developing agents have been sought that would unblock under preselected conditions of development after which such developing agents would be free to participate in image-forming (dye or silver metal forming) reactions.

U.S. Pat. No. 3,342,599 to Reeves discloses the use of Schiff-base developer precursors. Schleigh and Faul, in a *Research Disclosure* (129 (1975) pp. 27-30), describes the quaternary blocking of color developers and the acetamido blocking of p-phenylenediamines. (All Research Disclosures referenced herein are published by Kenneth Mason Publications, Ltd., Dudley Annex, 12a North Street, Emsworth, Hampshire P010 7DQ, ENGLAND.) Subsequently, U.S. Pat. No. 4,157,915 to Hamaoka et al. and U.S. Pat. No. 4,060,418 to Waxman and Mouming describe the preparation and use of blocked p-phenylenediamines in an image-receiving sheet for color diffusion transfer.

All of these approaches have failed in practical product applications because of one or more of the following problems: desensitization of sensitized silver halide; unacceptably slow unblocking kinetics; instability of blocked developer yielding increased fog and/or decreased Dmax after storage, lack of simple methods for releasing the blocked developer, inadequate or poor image formation, and other problems. Especially in the area of photothermographic color films, other potential problems include poor discrimination and poor dye-forming activity.

Recent developments in blocking and switching chemistry have led to blocked developing agents, including p-phenylenediamines, that perform relatively well. In particular, compounds having "β-ketoester" type blocking groups (strictly, β-ketoacyl blocking groups) are described in U.S. Pat. No. 5,019,492. With the advent of the β-ketoester blocking chemistry, it has become possible to incorporate p-phenylenediamine developers in film systems in a form from which they only become active when required for development. The β-ketoacyl blocked developers are released from the film layers in which they are incorporated by an alkaline developing solution containing a dinucleophile, for example hydroxylamine.

In addition to the aforementioned U.S. Pat. No. 4,157,915, blocked developing agents involving β-elimination reactions during unblocking have been disclosed in European Patent Application 393523 and kokais 57076453; 2131253; and 63123046, the latter specifically in the context of photothermographic elements.

The incorporation of blocked developers in photographic elements is typically carried out using colloidal gelatin dispersions of the blocked developers. These dispersions are prepared using means well known in the art, wherein the developer precursor is dissolved in a high vapor pressure organic solvent (for example, ethyl acetate), along with, in some cases, a low vapor pressure organic solvent (such as dibutylphthalate), and then emulsified with an aqueous surfactant and gelatin solution. After emulsification, usually done with a colloid mill, the high vapor pressure organic solvent is removed by evaporation or by washing, as is well known in the art. Alternatively, solid particle (ball-milled) dispersions can be prepared using means well known in the art, typically by shaking a suspension of the material with zirconia beads and a surfactant in water until sufficiently small particle size is produced.

There remains a need for blocked photographically useful compounds with good keeping properties, which at the same time exhibit good unblocking kinetics. With respect to developing agents, it is an object to obtain a film incorporating blocked developing agents that provide good dye-forming activity and which, at the same time, yield little or no increased fog and/or provide little or no decrease in Dmax after storage.

In one application of the invention, it is a further object to obtain blocked photographically useful agents for use in photothermographic color films. With respect to developing agents, there is a continuing need for photothermographic imaging elements that contain a developing agent in a form that is stable until development yet can rapidly and easily develop the imaging element once processing has been initiated by heating the element and/or by applying a processing solution, such as a solution of a base or acid or pure water, to the element. A completely dry or apparently dry process is most desirable. The existence of such a process would allow for very rapidly processed films that can be processed simply and efficiently in photoprocessing kiosks. Such kiosks, with increased numbers and accessibility, could ultimately allow for, relatively speaking, anytime and anywhere silver-halide film development.

Similarly, there is a need for incorporating other photographically useful compounds into a photothermographic element such that they remain stable until processing and are then rapidly released. Such photographically useful compounds include, couplers, dyes and dye precursors, electron transfer agents, development inhibitors, etc., as discussed more fully below. The blocking of other photographically useful compounds, besides developing agents, are disclosed in the prior art. For example, U.S. Pat. No. 5,283,162 to Kapp et al. and U.S. Pat. No. 4,546,073 to Bergthaller disclose blocked development inhibitors, and U.S. Pat. No. 4,248,962 to Lau discloses blocked couplers wherein the blocking group in turn comprises a photographically useful group.

SUMMARY OF THE INVENTION

This invention relates to a blocked compound that decomposes (i.e., unblocks) on thermal activation by a 1,2 elimination mechanism to release a photographically useful group (also referred to herein as a PUG). In a preferred embodiment, the photographically useful group is a developing agent.

In one embodiment, thermal activation preferably occurs at temperatures between about 100 and 180° C. In another embodiment, thermal activation preferably occurs at temperatures between about 20 and 140 ° C. in the presence of added acid, base and/or water.

The invention further relates to a light sensitive photographic element comprising a support and a blocked compound that decomposes on thermal activation by a 1,2 elimination mechanism to release a photographically useful group.

The invention additionally relates to a method of image formation having the steps of: thermally developing an imagewise exposed photographic element having a blocked compound (for example, a blocked developer) that decomposes on thermal activation by a 1,2 elimination mechanism to release a photographically useful group to form a developed image, scanning said developed image to form a first electronic image representation (or "electronic record") from said developed image, digitizing said first electronic record to form a digital image, modifying said digital image to form a second electronic image representation, and storing, transmitting, printing or displaying said second electronic image representation.

The invention further relates to a one-time use camera having a light sensitive photographic element comprising a support and a blocked compound that decomposes by a 1,2 elimination mechanism to release a photographically useful group on thermal activation. The invention further relates to a method of image formation having the steps of imagewise exposing such a light sensitive photographic element in a one-time-use camera having a heater and thermally processing the exposed element in the camera.

The improvements were achieved by a compound represented by Structure I below, in which the methylsulfonyl group is substituted with an electron withdrawing group.

I

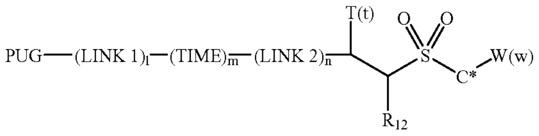

wherein:

PUG is a photographically useful group;

LINK 1 and LINK 2 are linking groups;

TIME is a timing group;

1 is 0 or 1;

m is 0, 1, or 2;

n is 0or 1;

$1+n \geqq 0$;

w is 1 or2;

t is 0, 1, or 2, and when t is not 2, the necessary number of hydrogens are present instead of T groups;

T is independently selected from a substituted or unsubstituted (referring to the following T groups) alkyl group, cycloalkyl group, aryl, or heterocyclic group, an inorganic monovalent electron withdrawing group, or an inorganic divalent electron withdrawing group capped with at least one C1 to C10 organic group (either an $R_{13}$ or an $R_{13}$ and $R_{14}$ group), preferably capped with a substituted or unsubstituted alkyl or aryl group; or T is joined with W, C* or $R_{12}$ to form a ring; or two T groups can combine to form a ring;

$R_{12}$ is hydrogen, or a substituted or unsubstituted alkyl, cycloalkyl, aryl, or heterocyclic group;

C* is a tetrahedral carbon;

W is independently selected from a monovalent electron withdrawing group, a divalent electron withdrawing group, an aryl group substituted with one to seven electron withdrawing groups, or a substituted or unsubstituted heteroaromatic group; when W is a divalent electron withdrawing group, an aryl group, or a heteroaromatic group, it can combine with C*, $R_{12}$, or T to form a ring; when w is 2, the two W groups can optionally form a ring; and when w is 1, the C* may be attached to one or two hydrogen atoms or to one hydrogen atom and one substituted or unsubstituted alkyl group that is not an electron withdrawing group or aryl group that is not substituted with an electron-withdrawing group;

Preferably, T is an inorganic electron withdrawing group such as halogen, $—NO_2$, or —CN, when it is monovalent, or a heteroaromatic group. Preferably, when T is divalent, it is an inorganic electron withdrawing group capped by $R_{13}$ (or by $R_{13}$ and $R_{14}$), for example $—SO_2R_{13}$, $—OSO_2R_{13}$, $—NR_{13}(SO_2R_{14})$, $—CO_2R_{13}$, $—COR_{13}$, $—NR_{13}(COR_{14})$, etc., wherein $R_{13}$ and $R_{14}$ can be independently selected from a substituted or unsubstituted (referring to the following groups) alkyl, aryl, or heterocyclic group, preferably having 1 to 10 carbon atoms. Preferably, when T is an alkyl or aryl group it is substituted with electron withdrawing groups, for example $—CF_3$ and, in the case of aryl, substituted with up to seven electron withdrawing groups.

Preferably, when it is a monovalent electron withdrawing group, W is an inorganic group such as halogen, $—NO_2$, —CN, or a halogenated alkyl group, e.g., $—CF_3$. When W is a divalent electron withdrawing group, it is preferably an inorganic group capped by $R_{13}$ or by $R_{13}$ and $R_{14}$, for example $—SO_2R_{13}$, $—OSO_2R_{13}$, $—NR_{13}(SO_2R_{14})$, $—CO_2R_{13}$, $—COR_{13}$, $—NR_{13}(COR_{14})$, etc., wherein $R_{13}$ and $R_{14}$ can independently be selected from substituted or unsubstituted alkyl, aryl, or heterocyclic group, preferably having 1 to 6 carbon atoms, more preferably a phenyl or C1 to C6 alkyl group.

By the term inorganic is herein meant a group not containing carbon excepting carbonates, cyanides, and cyanates. The term heterocyclic herein includes aromatic and non-aromatic rings containing at least one (preferably 1 to 3) heteroatoms in the ring. If the named groups for a symbol such as W in Structure I apparently overlap, the narrower named group is excluded from the broader named group solely to avoid any such apparent overlap. Thus, for example, heteroaromatic groups in the definition of T may be electron withdrawing in nature, but are not included under monovalent or divalent electron withdrawing groups as they are defined herein.

When referring to electron withdrawing groups, this can be indicated or estimated by the Hammett substituent constants ($\sigma_p$, $\sigma_m$), as described by L. P. Hammett in Physical Organic Chemisty (McGraw-Hill Book Co., NY, 1940), or by the Taft polar substituent constants ($\sigma_I$) as defined by R. W. Taft in Steric Effects in Organic Chemistry (Wiley and Sons, NY, 1956), and in other standard organic textbooks. The $\sigma_p$ and $\sigma_m$ parameters, which were used first to characterize the ability of benzene ring-substituents (in the para or meta position) to affect the electronic nature of a reaction site, were originally quantified by their effect on the pKa of benzoic acid. Subsequent work has extended and refined the original concept and data, and for the purposes of prediction and correlation, standard sets of $\sigma_p$ and $\sigma_m$ are widely available in the chemical literature, as for example in C. Hansch et al., J. Med. Chem., 17, 1207 (1973). For substituents attached to a tetrahedral carbon instead of aryl groups, the inductive substituent constant $\sigma_I$ is herein used to characterize the electronic property. Preferably, an electron withdrawing group on an aryl ring has a $\sigma_p$ or $\sigma_m$ of greater than zero, more preferably greater than 0.05, most preferably greater than 0.1. The $\sigma_p$ is used to define electron withdrawing groups on aryl groups when the substituent is neither para nor meta. Similarly, an electron withdrawing group on a tetrahedral carbon preferably has a $\sigma_I$ of greater than zero, more preferably greater than 0.05, and most preferably greater than 0.1. In the event of a divalent group such as —$SO_2$—, the $\sigma_I$ is for the methyl substituted analogue such as —$SO_2CH_3$ ($\sigma_I$=+0.59). When more than one electron withdrawing group is present, then the summation of the substituent constants is used to estimate or characterize the total effect of the substituents.

In a preferred embodiment of the invention, LINK 1 and LINK 2 are of structure II:

II

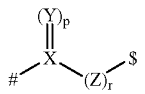

wherein

X represents carbon or sulfur;

Y represents oxygen, sulfur or N—$R_1$, where $R_1$, is substituted or unsubstituted alkyl or substituted or unsubstituted aryl;

p is 1 or 2;

Z represents carbon, oxygen or sulfur;

r is 0 or 1;

with the proviso that when X is carbon, both p and r are 1, when X is sulfur, Y is oxygen, p is 2 and r is 0;

# denotes the bond to PUG (for LINK 1) or TIME (for LINK 2):

$ denotes the bond to TIME (for LINK 1) or $T_{(t)}$ substituted carbon (for LINK 2).

DETAILED DESCRIPTION OF THE INVENTION

Figure 1:
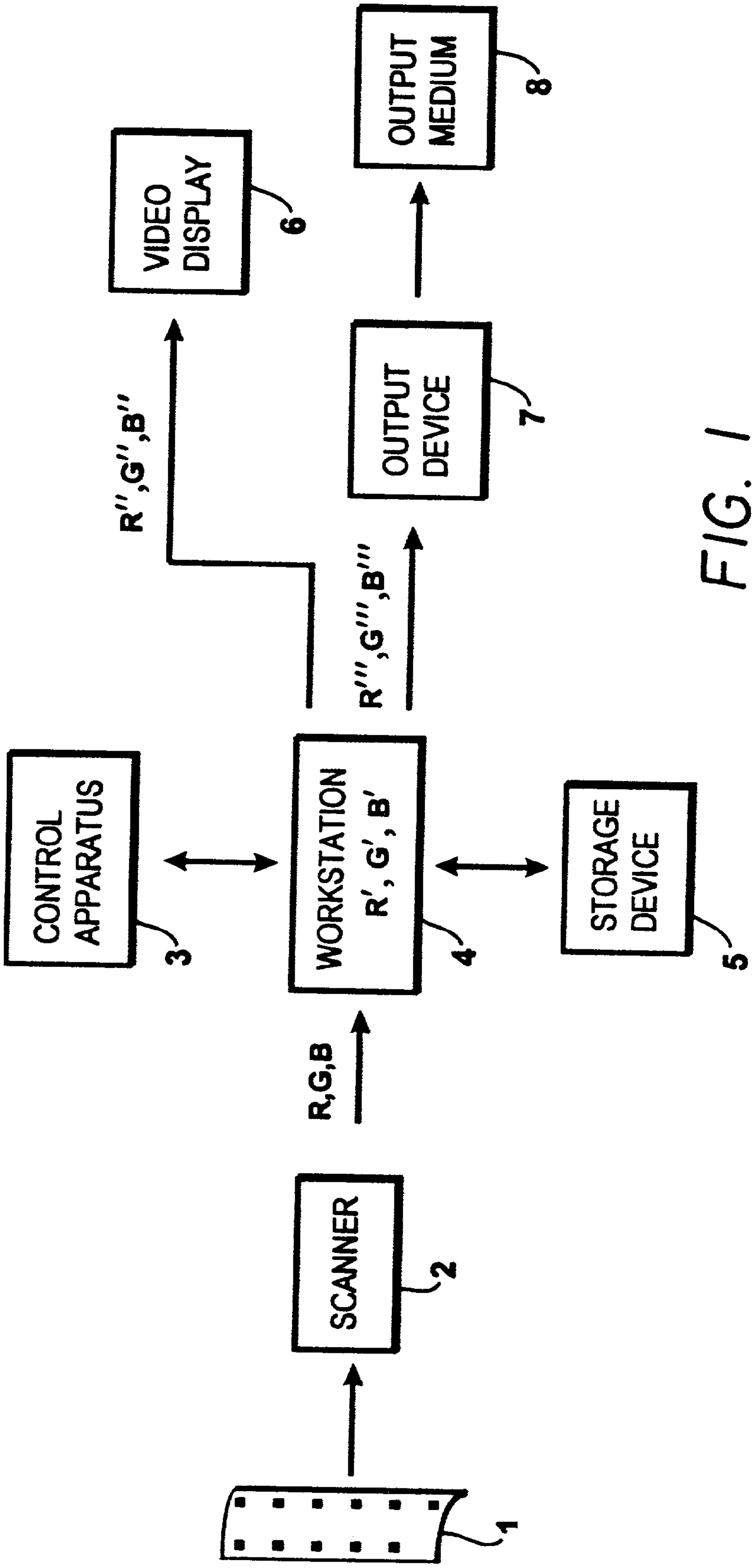
FIG. 1 shows in block diagram form an apparatus for processing and viewing image formation obtained by scanning the elements of the invention.

In Structure I, the PUG can be, for example, a photographic dye or photographic reagent. A photographic reagent herein is a moiety that upon release further reacts with components in the photographic element. Such photographically useful groups include, for example, couplers (such as, image dye-forming couplers, development inhibitor releasing couplers, competing couplers, polymeric couplers and other forms of couplers), development inhibitors, bleach accelerators, bleach inhibitors, inhibitor releasing developers, dyes and dye precursors, developing agents (such as competing developing agents, dye-forming developing agents, developing agent precursors, and silver halide developing agents), silver ion fixing agents, electron transfer agents, silver halide solvents, silver halide complexing agents, reductones, image toners, pre-processing and post-processing image stabilizers, hardeners, tanning agents, fogging agents, ultraviolet radiation absorbers, nucleators, chemical and spectral sensitizers or desensitizers, surfactants, and precursors thereof and other addenda known to be useful in photographic materials.

The PUG can be present in the blocked compound as a preformed species or as a precursor. For example, a preformed development inhibitor may be bonded to the blocking group or the development inhibitor may be attached to a group that is released at a particular time and location in the photographic material. The PUG may be, for example, a preformed dye or a compound that forms a dye after release from the blocking group.

In a preferred embodiment of the invention, the PUG is a developing agent. More preferably, the developing agent is a color developing agent. These include aminophenols, phenylenediamines, hydroquinones, pyrazolidinones, and hydrazines. Illustrative developing agents are described in U.S. Pat. Nos. 2,193,015, 2,108,243, 2,592,364, 3,656,950, 3,658,525, 2,751,297, 2,289,367, 2,772,282, 2,743,279, 2,753,256, and 2,304,953, the entire disclosures of which are incorporated herein by reference.

Illustrative PUG groups that are useful as developers are:

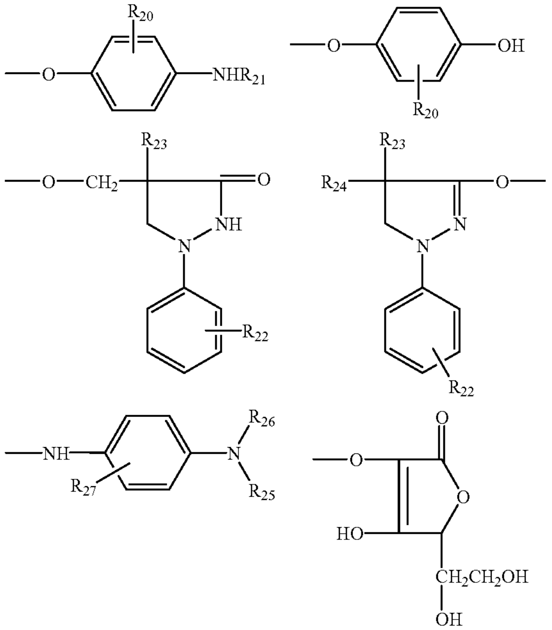

wherein $R_{20}$ is hydrogen, halogen, alkyl or alkoxy;

$R_{21}$ is a hydrogen or alkyl;

$R_{22}$ is hydrogen, alkyl, alkoxy or alkenedioxy; and $R_{23}$, $R_{24}$, $R_{25}$ $R_{26}$ and $R_{27}$ are hydrogen alkyl, hydroxyalkyl or sulfoalkyl.

As mentioned above, in a preferred embodiment of the invention, LINK 1 or LINK 2 are of structure II:

II

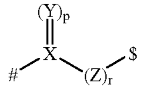

wherein

X represents carbon or sulfur;

Y represents oxygen, sulfur or N—$R_1$, where $R_1$ is substituted or unsubstituted alkyl or substituted or unsubstituted aryl;

p is 1 or 2;

Z represents carbon, oxygen or sulfur;

r is 0 or 1;

with the proviso that when X is carbon, both p and r are 1, when X is sulfur, Y is oxygen, p is 2 and r is 0;

# denotes the bond to PUG (for LINK 1) or TIME (for LINK 2):

$ denotes the bond to TIME (for LINK 1) or $T_{(t)}$ substituted carbon (for LINK 2).

Illustrative linking groups include, for example,

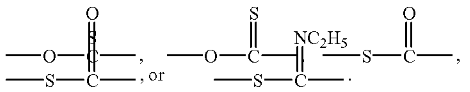

TIME is a timing group. Such groups are well-known in the art such as (1) groups utilizing an aromatic nucleophilic substitution reaction as disclosed in U.S. Pat. No. 5,262,291; (2) groups utilizing the cleavage reaction of a hemiacetal (U.S. Pat. No. 4,146,396, Japanese Applications 60-249148; 60-249149); (3) groups utilizing an electron transfer reaction along a conjugated system (U.S. Pat. Nos. 4,409,323; 4,421,845; Japanese Applications 57-188035; 58-98728; 58-209736; 58-209738); and (4) groups using an intramolecular nucleophilic substitution reaction (U.S. Pat. No. 4,248,962).

Illustrative timing groups are illustrated by formulae T-1 through T-4.

T-1

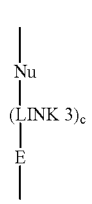

wherein:

Nu is a nucleophilic group;

E is an electrophilic group comprising one or more carbo- or hetero- aromatic rings, containing an electron deficient carbon atom;

LINK 3 is a linking group that provides 1 to 5 atoms in the direct path between the nucleopnilic site of Nu and the electron deficient carbon atom in E; and c is 0or 1.

Such timing groups include, for example:

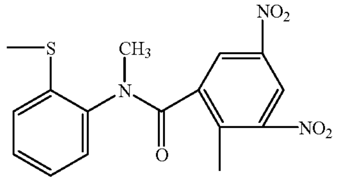

and

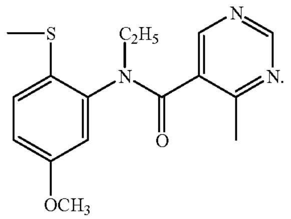

These timing groups are described more fully in U.S. Pat. No. 5,262,291, incorporated herein by reference.

T-2

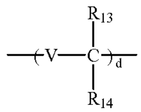

wherein

V represents an oxygen atom, a sulfur atom, or an

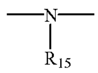

group;

$R_{13}$ and $R_{14}$ each represents a hydrogen atom or a substituent group;

$R_{15}$ represents a substituent group; and d represents 1 or 2.

Typical examples of $R_{13}$ and $R_{14}$, when they represent substituent groups, and $R_{15}$ include

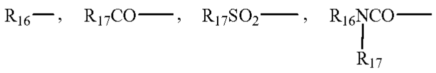

and

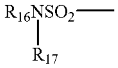

where, $R_{16}$ represents an aliphatic or aromatic hydrocarbon residue, or a heterocyclic group; and $R_{17}$ represents a hydrogen atom, an aliphatic or aromatic hydrocarbon residue, or a heterocyclic group, $R_{13}$, $R_{14}$ and $R_{15}$ each may represent a divalent group, and any two of them combine with each other to complete a ring structure. Specific examples of the group represented by formula (T-2) are illustrated below.

T-3

—OCH2—,

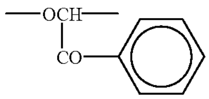

,

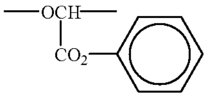

,

—SCH2—,

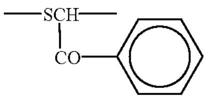

,

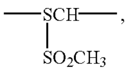

,

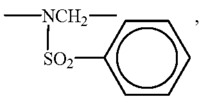

,

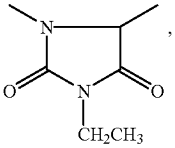

, and

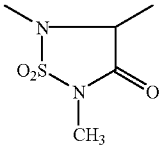

—Nu1—LINK4—E1— wherein Nu1 represents a nucleophilic group, and an oxygen or sulfur atom can be given as an example of nucleophilic species; E1 represents an electrophilic group being a group which is subjected to nucleophilic attack by Nu1; and LINK4 represents a linking group which enables Nu1 and E1 to have a steric arrangement such that an intramolecular nucleophilic substition reaction can occur. Specific examples of the group represented by formula (T-3) are illustrated below.

T-4

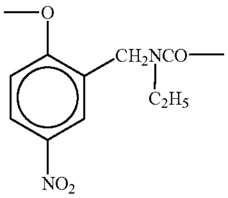

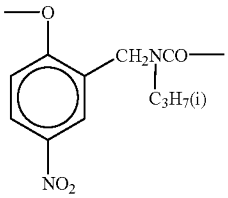

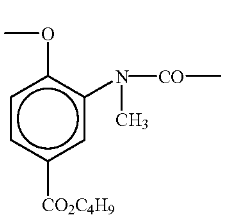

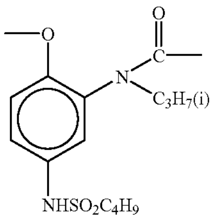

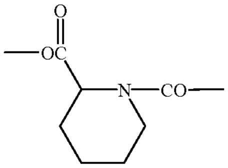

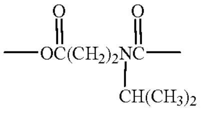

-continued

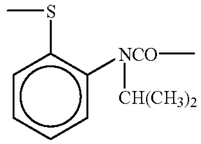

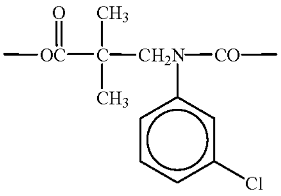

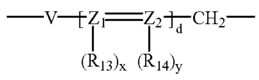

wherein V, $R_{13}$, $R_{14}$ and d all have the same meaning as in formula (T-2), respectively. In addition, $R_{13}$ and $R_{14}$ may be joined together to form a benzene ring or a heterocyclic ring, or V may be joined with $R_{13}$ or $R_{14}$ to form a benzene or heterocyclic ring. $Z_1$ and $Z_2$ each independently represents a carbon atom or a nitrogen atom, and x and y each represents 0 or 1.

Specific examples of the timing group (T-4) are illustrated below.

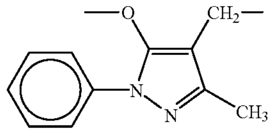

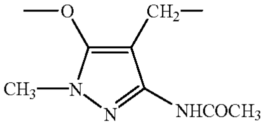

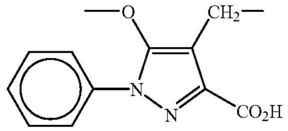

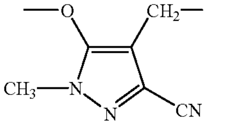

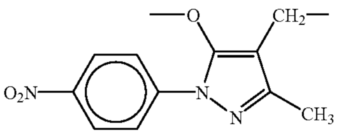

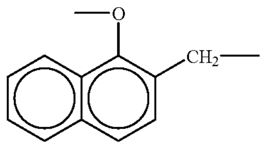

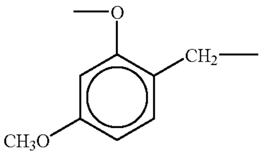

-continued

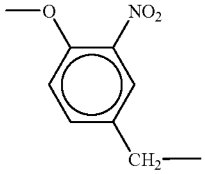

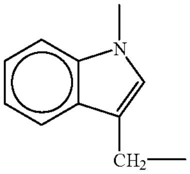

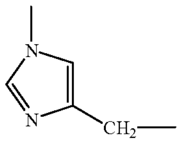

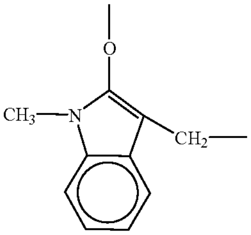

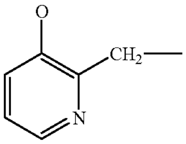

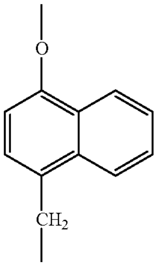

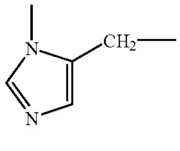

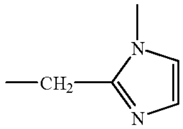

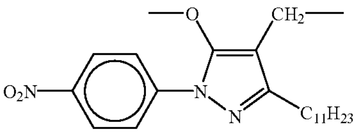

-continued

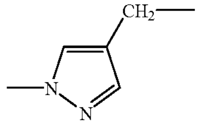

Particularly preferred photographically useful compounds are blocked developers shown in FIG. II:

FIG. II

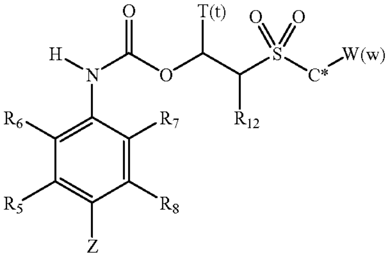

wherein:

Z is OH or $NR_2R_3$, where $R_2$ and $R_3$ are independently hydrogen or a substituted or unsubstituted alkyl group or $R_2$ and $R_3$ are connected to form a ring;

$R_5$, $R_6$, $R_7$, and $R_8$ are independently hydrogen, halogen, hydroxy, amino, alkoxy, carbonamido, sulfonamido, alkylsulfonamido or alkyl, or $R_5$ can connect with $R_3$ or $R_6$ and/or $R_8$ can connect to $R_2$ or $R_7$ to form a ring;

t is0, 1,or2;

w is 1 or2;

T is independently selected from a substituted or unsubstituted (referring to the following T groups) alkyl group, cycloalkyl group, aryl, or heterocyclic group, an inorganic monovalent electron withdrawing group, or an inorganic divalent electron withdrawing group capped with an $R_{13}$ group (or with an $R_{13}$ and $R_{14}$ group), preferably capped with a substituted or unsubstituted alkyl or aryl group; or T is joined with W, C* or $R_{12}$ to form a ring; when t is 2, two T groups can optionally combine to form a ring; when t is less than 2, the necessary number of hydrogens (2-t) are present instead;

$R_{12}$ is hydrogen, or a substituted or unsubstituted alkyl, cycloalkyl, aryl or heterocyclic group;

C* is a tetrahedral carbon;

W is independently selected from a monovalent electron withdrawing group, a divalent electron withdrawing group, an aryl group substituted with one to seven electron withdrawing groups, or a substituted or unsubstituted heteroaromatic group; when W is a divalent electron withdrawing group, an aryl group, or a heteroaromatic group, it can combine with C*, $R_{12}$, or T to form a ring; when w is 2, the two W groups can form a ring; and C* may be attached to one or two hydrogen atoms or to one hydrogen atom and one substituted or unsubsituted alkyl group that is not an electron withdrawing group or an aryl group that is not substituted with an electron-withdrawing group;

Preferably, T is an inorganic group such as halogen, —$NO_2$, or —CN when it is monovalent. Preferably, when T is a divalent inorganic electron withdrawing group, it is one capped by $R_{13}$ (or by $R_{13}$ and $R_{14}$), for example —$SO_2R_{13}$, —$OSO_2R_{13}$, —$NR_{13}(SO_2R_{14})$, —$CO_2R_{13}$, —$COR_{13}$, —$NR_{13}(COR_{14})$, etc., wherein $R_{13}$ and $R_{14}$ can be independently selected from a substituted or unsubstituted alkyl, aryl, or heterocyclic group, preferably having 1 to 6 carbon atoms.

Preferably, when T is an alkyl or aryl group it is substituted with electron withdrawing groups, for example —$CF_3$ and, in the case of aryl, substituted with up to seven electron withdrawing groups. Other preferred T groups are heteroaromatic groups.

Preferably, W is an inorganic group such as halogen, —$NO_2$, —CN, or a halogenated alkyl group, e.g., —$CF_3$, when it is a monovalent electron withdrawing group. Preferably, when W is a divalent electron withdrawing group, it is an inorganic group capped by $R_{13}$ or by $R_{13}$ and $R_{14}$, for example, —$SO_2R_{13}$, —$OSO_2R_{13}$, $NR_{13}(SO_2R_{14})$, —$CO_2R_{13}$, —$COR_{13}$, —$NR_{13}(COR_{14})$, etc., wherein $R_{13}$ and $R_{14}$ can be independently selected from a substituted or unsubstituted alkyl, aryl, or heterocyclic group, preferably having 1 to 6 carbon atoms.

Heteroaromatic groups useful in compounds of Structure I and III are preferably a 5- or 6-membered heterocyclic rings containing one or more hetero atoms, such as N, O, S or Se. Such groups include for example substituted or unsubstituted benzimidazolyl, benzothiazolyl, benzoxazolyl, benzothienyl, benzofuryl, furyl, imidazolyl, indazolyl, indolyl, isoquinolyl, isothiazolyl, isoxazolyl, oxazolyl, picolinyl, purinyl, , pyranyl, pyrazinyl, pyrazolyl, pyridyl, pyrimidinyl, pyrrolyl, quinaldinyl, quinazolinyl, quinolyl, quinoxalinyl, tetrazolyl, thiadiazolyl, thiatriazolyl, thiazolyl, thienyl, and triazolyl groups.

When reference in this application is made to a particular moiety or group, "substituted or unsubstituted" means that the moiety may be unsubstituted or substituted with one or more substituents (up to the maximum possible number), for example, substituted or unsubstituted alkyl, substituted or unsubstituted benzene (with up to five substituents), substituted or unsubstituted heteroaromatic (with up to five substituents), and substituted or unsubstituted heterocyclic (with up to five substitutuents). Generally, unless otherwise specifically stated, substituent groups usable on molecules herein include any groups, whether substituted or unsubstituted, which do not destroy properties necessary for the photographic utility. Examples of substituents on any of the mentioned groups can include known substituents, such as: halogen, for example, chloro, fluoro, bromo, iodo; alkoxy, particularly those "lower alkyl" (that is, with 1 to 6 carbon atoms), for example, methoxy, ethoxy; substituted or unsubstituted alkyl, particularly lower alkyl (for example, methyl, trifluoromethyl); thioalkyl (for example, methylthio or ethylthio), particularly either of those with 1 to 6 carbon atoms; substituted and unsubstituted aryl, particularly those having from 6 to 20 carbon atoms (for example, phenyl); and substituted or unsubstituted heteroaryl, particularly those having a 5 or 6-membered ring containing 1 to 3 heteroatoms selected from N, O, or S (for example, pyridyl, thienyl, furyl, pyrrolyl); acid or acid salt groups such as any of those described below; and others known in the art. Alkyl substituents may specifically include "lower alkyl" (that is, having 1-6 carbon atoms), for example, methyl, ethyl, and the like. Further, with regard to any alkyl group or alkylene group, it will be understood that these can be branched, unbranched, or cyclic.

The following are representative examples of photographically useful compounds for use in the invention:

| Ex. | D94 | KAN | Structure |
| --- | --- | --- | --- |
| D-1 | | | 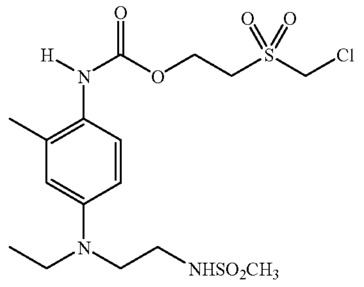 |
| D-2 | | | 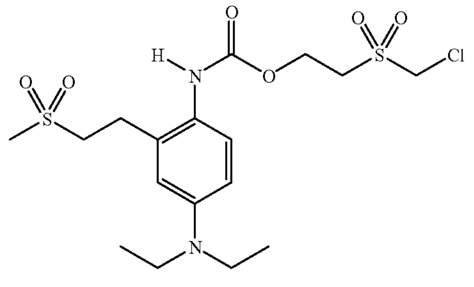 |

-continued
| Ex. | D94 | KAN | Structure |
|---|---|---|---|
| D-3 | JW | 766803-0 | 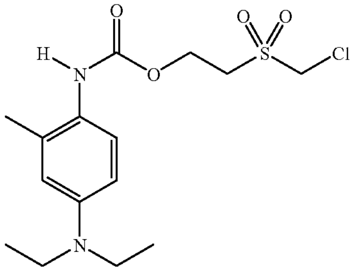 |
| D-4 | JS | 686952-6 | 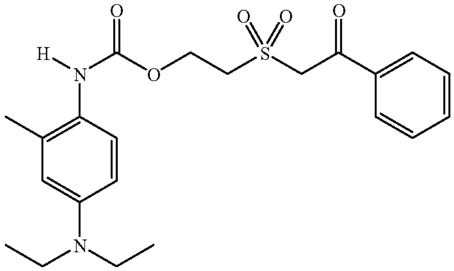 |
| D-5 | | | 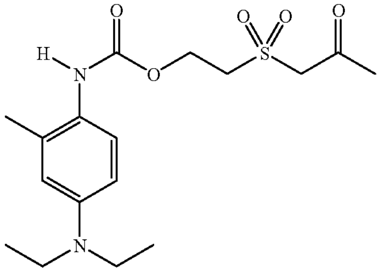 |
| D-6 | JU | 711747-4 | 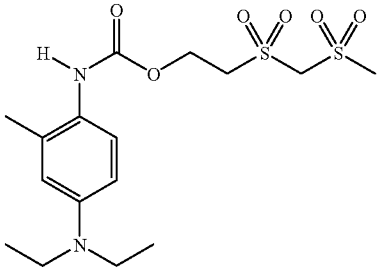 |
| D-7 | JB | 745782-8 | 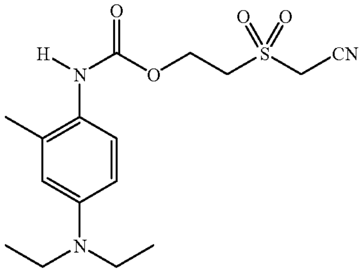 |

-continued
| Ex. | D94 | KAN | Structure |
|---|---|---|---|
| D-8 | JC | 738001-7 | 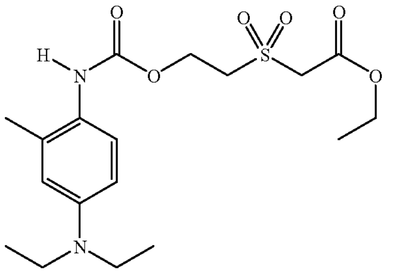 |
| D-9 | | | 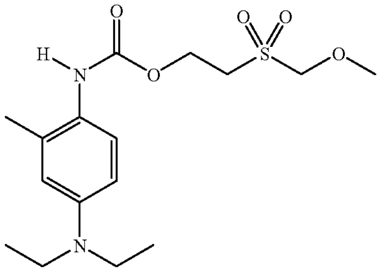 |
| D-10 | | | 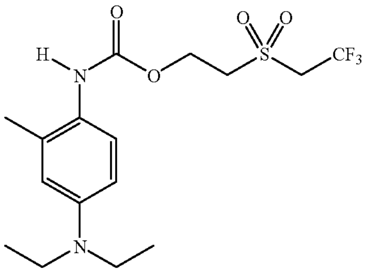 |
| D-11 | | | 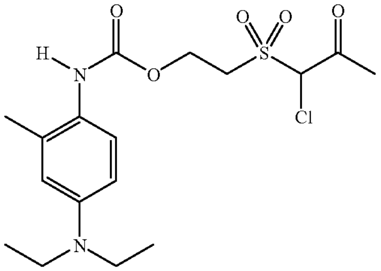 |
| D-12 | JQ | 725118-2 | 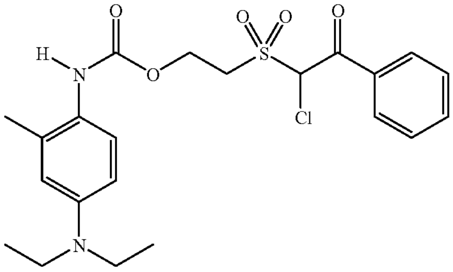 |

-continued
| Ex. | D94 | KAN | Structure |
|---|---|---|---|
| D-13 | | | 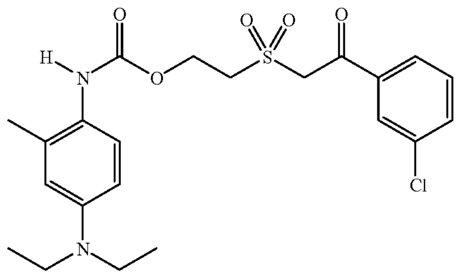 |
| D-14 | | | 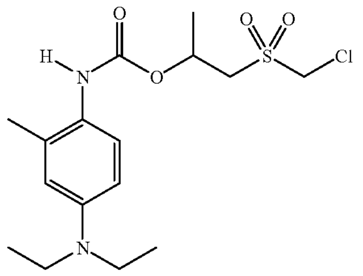 |
| D-15 | | | 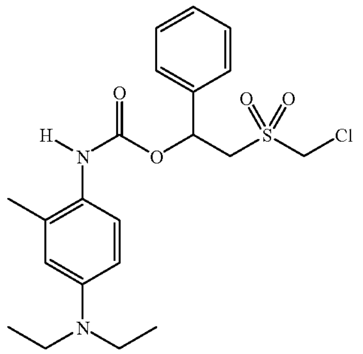 |
| D-16 | | | 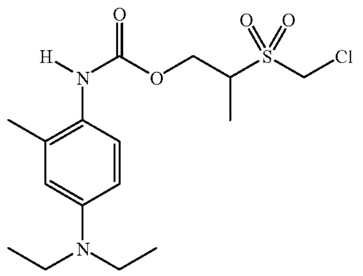 |
| D-17 | | | 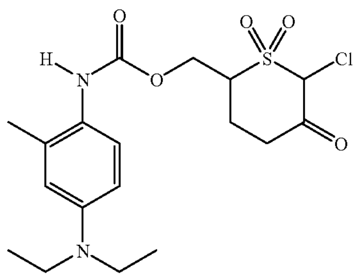 |

-continued
| Ex. | D94 | KAN | Structure |
|---|---|---|---|
| D-18 | | | 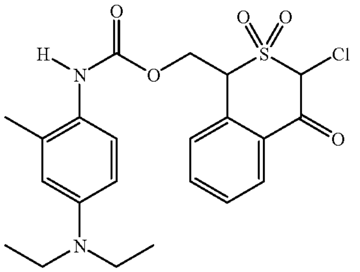 |
| D-19 | | | 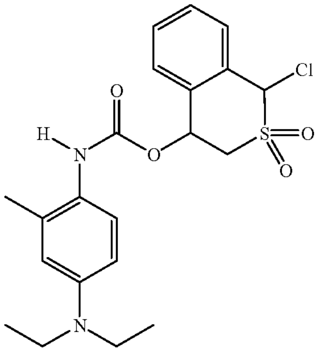 |
| D-20 | | | 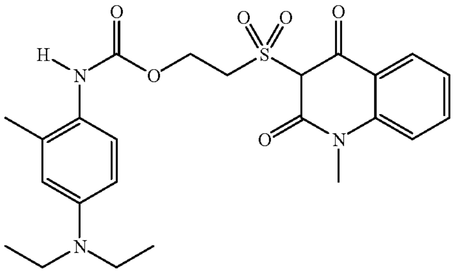 |
| D-21 | | | 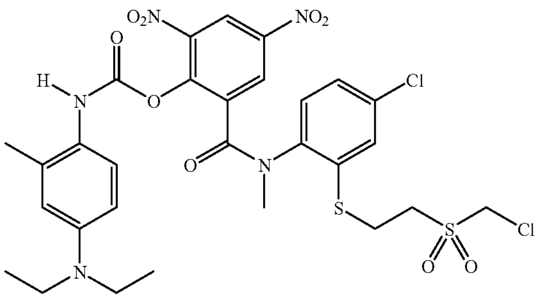 |
| D-21 | | | 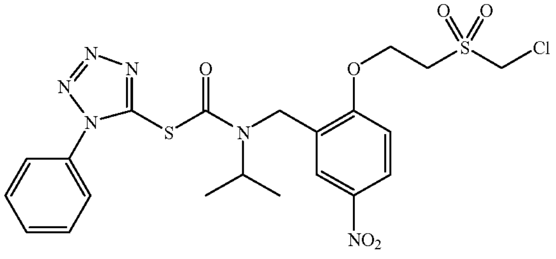 |

-continued
| Ex. | D94 | KAN | Structure |
|---|---|---|---|
| D-22 | | | 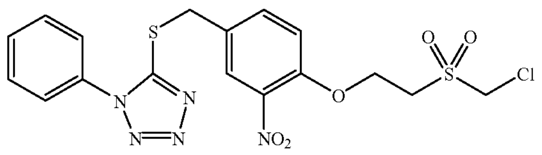 |
| D-23 | | | 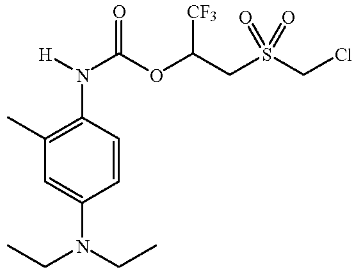 |
| D-24 | | | 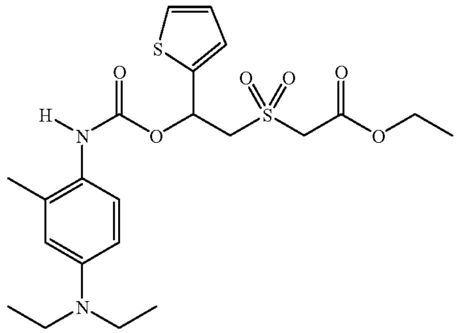 |
| D-25 | | | 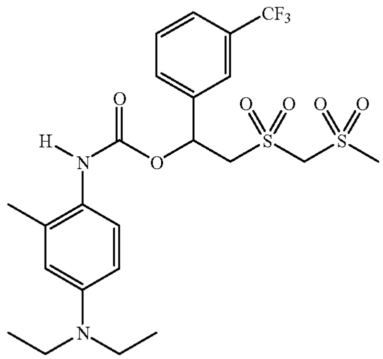 |
| D-26 | | | 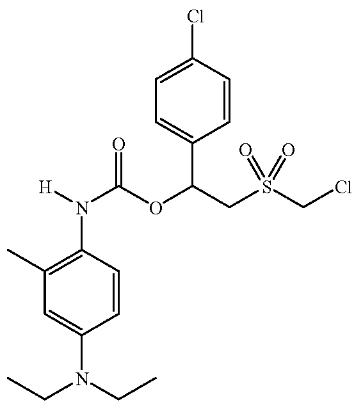 |

-continued

| Ex. | D94 | KAN | Structure |
|---|---|---|---|
| D-27 | | | 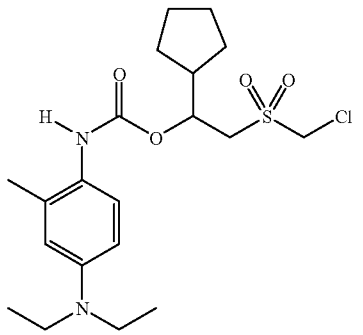 |

The blocked developer is preferably incorporated in one or more of the imaging layer of the imaging element. The amount of blocked developer used is preferably 0.01 to 5 $g/m^2$, more preferably 0.1to 2 $g/m^2$ and most preferably 0.3 to 2$g/m^2$ in each layer to which it is added. These may be color forming or non-color forming layers of the element. The blocked developer can be contained in a separate element that is contacted to the photographic element during processing.

After image-wise exposure of the imaging element, the blocked developer is activated during processing of the imaging element by the presence of acid or base in the processing solution, by heating the imaging element during processing of the imaging element, and/or by placing the imaging element in contact with a separate element, such as a laminate sheet, during processing. The laminate sheet optionally contains additional processing chemicals such as those disclosed in Sections XIX and XX of *Research Disclosure*, September 1996, Number 389, Item 38957 (hereafter referred to as ("*Research Disclosure* I "). All sections referred to herein are sections of *Research Disclosure* I, unless otherwise indicated. Such chemicals include, for example, sulfites, hydroxyl amine, hydroxamic acids and the like, antifoggants, such as alkali metal halides, nitrogen containing heterocyclic compounds, and the like, sequestering agents such as an organic acids, and other additives such as buffering agents, sulfonated polystyrene, stain reducing agents, biocides, desilvering agents, stabilizers and the like.

The blocked compounds may be used in any form of photographic system. A typical color negative film construction useful in the practice of the invention is illustrated by the following element, SCN-1:

| Element SCN-1 | |
|---|---|
| Soc | Surface Overcoat |
| BU | Blue Recording Layer Unit |
| IL1 | First Interlayer |
| GU | Green Recording Layer Unit |
| 1L2 | Second Interlayer |
| RU | Red Recording Layer Unit |
| AHU | Antihalation Layer Unit |
| S | Support |
| SOC | Surface Overcoat |

The support S can be either reflective or transparent, which is usually preferred. When reflective, the support is white and can take the form of any conventional support currently employed in color print elements. When the support is transparent, it can be colorless or tinted and can take the form of any conventional support currently employed in color negative elements—e.g., a colorless or tinted transparent film support. Details of support construction are well understood in the art. Examples of useful supports are poly(vinylacetal) film, polystyrene film, poly(ethyleneterephthalate) film, poly (ethylene naphthalate) film, polycarbonate film, and related films and resinous materials, as well as paper, cloth, glass, metal, and other supports that withstand the anticipated processing conditions. The element can contain additional layers, such as filter layers, interlayers, overcoat layers, subbing layers, antihalation layers and the like. Transparent and reflective support constructions, including subbing layers to enhance adhesion, are disclosed in Section XV of *Research Disclosure* I.

Photographic elements of the present invention may also usefully include a magnetic recording material as described in *Research Disclosure*, Item 34390, November 1992, or a transparent magnetic recording layer such as a layer containing magnetic particles on the underside of a transparent support as in U.S. Pat. Nos. 4,279,945, and 4,302,523.

Each of blue, green and red recording layer units BU, GU and RU are formed of one or more hydrophilic colloid layers and contain at least one radiation-sensitive silver halide emulsion and coupler, including at least one dye image-forming coupler. It is preferred that the green, and red recording units are subdivided into at least two recording layer sub-units to provide increased recording latitude and reduced image granularity. In the simplest contemplated construction each of the layer units or layer sub-units consists of a single hydrophilic colloid layer containing emulsion and coupler. When coupler present in a layer unit or layer sub-unit is coated in a hydrophilic colloid layer other than an emulsion containing layer, the coupler containing hydrophilic colloid layer is positioned to receive oxidized color developing agent from the emulsion during development. Usually the coupler containing layer is the next adjacent hydrophilic colloid layer to the emulsion containing layer.

In order to ensure excellent image sharpness, and to facilitate manufacture and use in cameras, all of the sensitized layers are preferably positioned on a common face of the support. When in spool form, the element will be spooled such that when unspooled in a camera, exposing light strikes all of the sensitized layers before striking the face of the support carrying these layers. Further, to ensure excellent sharpness of images exposed onto the element, the total thickness of the layer units above the support should be controlled. Generally, the total thickness of the sensitized layers, interlayers and protective layers on the exposure face of the support are less than 35 μm.

Any convenient selection from among conventional radiation-sensitive silver halide emulsions can be incorporated within the layer units and used to provide the spectral absorptances of the invention. Most commonly high bromide emulsions containing a minor amount of iodide are employed. To realize higher rates of processing, high chloride emulsions can be employed. Radiation-sensitive silver chloride, silver bromide, silver iodobromide, silver iodochloride, silver chlorobromide, silver bromochloride, silver iodochlorobromide and silver iodobromochloride grains are all contemplated. The grains can be either regular or irregular (e.g., tabular). Tabular grain emulsions, those in which tabular grains account for at least 50 (preferably at least 70 and optimally at least 90) percent of total grain projected area are particularly advantageous for increasing speed in relation to granularity. To be considered tabular a grain requires two major parallel faces with a ratio of its equivalent circular diameter (ECD) to its thickness of at least 2. Specifically preferred tabular grain emulsions are those having a tabular grain average aspect ratio of at least 5 and, optimally, greater than 8. Preferred mean tabular grain thicknesses are less than 0.3 μm (most preferably less than 0.2 μm). Ultrathin tabular grain emulsions, those with mean tabular grain thicknesses of less than 0.07 μm, are specifically contemplated. The grains preferably form surface latent images so that they produce negative images when processed in a surface developer in color negative film forms of the invention.

Illustrations of conventional radiation-sensitive silver halide emulsions are provided by *Research Disclosure* I, cited above, I. Emulsion grains and their preparation. Chemical sensitization of the emulsions, which can take any conventional form, is illustrated in section IV. Chemical sensitization. Compounds useful as chemical sensitizers, include, for example, active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 4 to 8, and temperatures of from 30 to 80° C. Spectral sensitization and sensitizing dyes, which can take any conventional form, are illustrated by section V. Spectral sensitization and desensitization. The dye may be added to an emulsion of the silver halide grains and a hydrophilic colloid at any time prior to (e.g., during or after chemical sensitization) or simultaneous with the coating of the emulsion on a photographic element. The dyes may, for example, be added as a solution in water or an alcohol or as a dispersion of solid particles. The emulsion layers also typically include one or more antifoggants or stabilizers, which can take any conventional form, as illustrated by section VII. Antifoggants and stabilizers.

The silver halide grains to be used in the invention may be prepared according to methods known in the art, such as those described in *Research Disclosure* I, cited above, and James, The Theory of the Photographic Process. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

In the course of grain precipitation one or more dopants (grain occlusions other than silver and halide) can be introduced to modify grain properties. For example, any of the various conventional dopants disclosed in *Research Disclosure* I, Section I. Emulsion grains and their preparation, subsection G. Grain modifying conditions and adjustments, paragraphs (3), (4) and (5), can be present in the emulsions of the invention. In addition it is specifically contemplated to dope the grains with transition metal hexacoordination complexes containing one or more organic ligands, as taught by Olm et al U.S. Pat. No. 5,360,712, the disclosure of which is here incorporated by reference.

It is specifically contemplated to incorporate in the face centered cubic crystal lattice of the grains a dopant capable of increasing imaging speed by forming a shallow electron trap (hereinafter also referred to as a SET) as discussed in *Research Disclosure* Item 36736 published November 1994, here incorporated by reference.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), deionized gelatin, gelatin derivatives (e.g., acetylated gelatin, phthalated gelatin, and the like), and others as described in *Research Disclosure*, I. Also useful as vehicles or vehicle extenders are hydrophilic water-penneable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers. The vehicle can be present in the emulsion in any amount useful in photographic emulsions. The emulsion can also include any of the addenda known to be useful in photographic emulsions.

While any useful quantity of light sensitive silver, as silver halide, can be employed in the elements useful in this invention, it is preferred that the total quantity be less than 10 $g/m^2$ of silver. Silver quantities of less than 7 $g/m^2$ are preferred, and silver quantities of less than 5 $g/m^2$ are even more preferred. The lower quantities of silver improve the optics of the elements, thus enabling the production of sharper pictures using the elements. These lower quantities of silver are additionally important in that they enable rapid development and desilvering of the elements. Conversely, a silver coating coverage of at least 1.5 g of coated silver per $m^2$ of support surface area in the element is necessary to realize an exposure latitude of at least 2.7 log E while maintaining an adequately low graininess position for pictures intended to be enlarged.

BU contains at least one yellow dye image-forming coupler, GU contains at least one magenta dye image-forming coupler, and RU contains at least one cyan dye image-forming coupler. Any convenient combination of conventional dye image-forming couplers can be employed. Conventional dye image-fonning couplers are illustrated by *Research Disclosure* I, cited above, X. Dye image formers and modifiers, B. Image-dye-forming couplers. The photographic elements may further contain other image-modifying compounds such as "Development Inhibitor-Releasing" compounds (DIR's). Useful additional DIR's for elements of the present invention, are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783;

3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference.

It is common practice to coat one, two or three separate emulsion layers within a single dye image-forming layer unit. When two or more emulsion layers are coated in a single layer unit, they are typically chosen to differ in sensitivity. When a more sensitive emulsion is coated over a less sensitive emulsion, a higher speed is realized than when the two emulsions are blended. When a less sensitive emulsion is coated over a more sensitive emulsion, a higher contrast is realized than when the two emulsions are blended. It is preferred that the most sensitive emulsion be located nearest the source of exposing radiation and the slowest emulsion be located nearest the support.

One or more of the layer units of the invention is preferably subdivided into at least two, and more preferably three or more sub-unit layers. It is preferred that all light sensitive silver halide emulsions in the color recording unit have spectral sensitivity in the same region of the visible spectrum. In this embodiment, while all silver halide emulsions incorporated in the unit have spectral absorptance according to invention, it is expected that there are minor differences in spectral absorptance properties between them. In still more preferred embodiments, the sensitizations of the slower silver halide emulsions are specifically tailored to account for the light shielding effects of the faster silver halide emulsions of the layer unit that reside above them, in order to provide an imagewise uniform spectral response by the photographic recording material as exposure varies with low to high light levels. Thus higher proportions of peak light absorbing spectral sensitizing dyes may be desirable in the slower emulsions of the subdivided layer unit to account for on-peak shielding and broadening of the underlying layer spectral sensitivity.

The interlayers IL1 and IL2 are hydrophilic colloid layers having as their primary function color contamination reduction—i.e., prevention of oxidized developing agent from migrating to an adjacent recording layer unit before reacting with dye-forming coupler. The interlayers are in part effective simply by increasing the diffusion path length that oxidized developing agent must travel. To increase the effectiveness of the interlayers to intercept oxidized developing agent, it is conventional practice to incorporate oxidized developing agent. Antistain agents (oxidized developing agent scavengers) can be selected from among those disclosed by *Research Disclosure* I, X. Dye image formers and modifiers, D. Hue modifiers/stabilization, paragraph (2). When one or more silver halide emulsions in GU and RU are high bromide emulsions and, hence have significant native sensitivity to blue light, it is preferred to incorporate a yellow filter, such as Carey Lea silver or a yellow processing solution decolorizable dye, in IL1. Suitable yellow filter dyes can be selected from among those illustrated by *Research Disclosure* I, Section VIII. Absorbing and scattering materials, B. Absorbing materials. In elements of the instant invention, magenta colored filter materials are absent from IL2 and RU.

The antihalation layer unit AHU typically contains a processing solution removable or decolorizable light absorbing material, such as one or a combination of pigments and dyes. Suitable materials can be selected from among those disclosed in *Research Disclosure* I, Section VIII. Absorbing materials. A common alternative location for AHU is between the support S and the recording layer unit coated nearest the support.

The surface overcoats SOC are hydrophilic colloid layers that are provided for physical protection of the color negative elements during handling and processing. Each SOC also provides a convenient location for incorporation of addenda that are most effective at or near the surface of the color negative element. In some instances the surface overcoat is divided into a surface layer and an interlayer, the latter functioning as spacer between the addenda in the surface layer and the adjacent recording layer unit. In another common variant form, addenda are distributed between the surface layer and the interlayer, with the latter containing addenda that are compatible with the adjacent recording layer unit. Most typically the SOC contains addenda, such as coating aids, plasticizers and lubricants, antistats and matting agents, such as illustrated by *Research Disclosure* I, Section IX. Coating physical property modifying addenda. The SOC overlying the emulsion layers additionally preferably contains an ultraviolet absorber, such as illustrated by *Research Disclosure* I, Section VI. UV dyes/optical brighteners/luminescent dyes, paragraph (1).

Instead of the layer unit sequence of element SCN-1, alternative layer units sequences can be employed and are particularly attractive for some emulsion choices. Using high chloride emulsions and/or thin (<0.2 μm mean grain thickness) tabular grain emulsions all possible interchanges of the positions of BU, GU and RU can be undertaken without risk of blue light contamination of the minus blue records, since these emulsions exhibit negligible native sensitivity in the visible spectrum. For the same reason, it is unnecessary to incorporate blue light absorbers in the interlayers.

When the emulsion layers within a dye image-fonning layer unit differ in speed, it is conventional practice to limit the incorporation of dye image-forming coupler in the layer of highest speed to less than a stoichiometric amount, based on silver. The function of the highest speed emulsion layer is to create the portion of the characteristic curve just above the minimum density—i.e., in an exposure region that is below the threshold sensitivity of the remaining emulsion layer or layers in the layer unit. In this way, adding the increased granularity of the highest sensitivity speed emulsion layer to the dye image record produced is minimized without sacrificing imaging speed.

In the foregoing discussion the blue, green and red recording layer units are described as containing yellow, magenta and cyan image dye-forming couplers, respectively, as is conventional practice in color negative elements used for printing. The invention can be suitably applied to conventional color negative construction as illustrated. Color reversal film construction would take a similar form, with the exception that colored masking couplers would be completely absent; in typical forms, development inhibitor releasing couplers would also be absent. In preferred embodiments, the color negative elements are intended exclusively for scanning to produce three separate electronic color records. Thus the actual hue of the image dye produced is of no importance.

What is essential is merely that the dye image produced in each of the layer units be differentiable from that produced by each of the remaining layer units. To provide this capability of differentiation it is contemplated that each of the layer units contain one or more dye image-forming couplers chosen to produce image dye having an absorption half-peak bandwidth lying in a different spectral region. It is immaterial whether the blue, green or red recording layer unit forms a yellow, magenta or cyan dye having an absorption half peak bandwidth in the blue, green or red region of the spectrum, as is conventional in a color negative element intended for use in printing, or an absorption half-peak bandwidth in any other convenient region of the spectrum, ranging from the near ultraviolet (300-400 nm) through the visible and through the near infrared (700-1200 nm), so long as the absorption half-peak bandwidths of the image dye in the layer units extend over substantially non-coextensive wavelength ranges. The term "substantially non-coextensive wavelength ranges" means that each image dye exhibits an absorption half-peak band width that extends over at least a 25 (preferably 50) nm spectral region that is not occupied by an absorption half-peak band width of another image dye. Ideally the image dyes exhibit absorption half-peak band widths that are mutually exclusive.

When a layer unit contains two or more emulsion layers differing in speed, it is possible to lower image granularity in the image to be viewed, recreated from an electronic record, by forming in each emulsion layer of the layer unit a dye image which exhibits an absorption half-peak band width that lies in a different spectral region than the dye images of the other emulsion layers of layer unit. This technique is particularly well suited to elements in which the layer units are divided into sub-units that differ in speed. This allows multiple electronic records to be created for each layer unit, corresponding to the differing dye images formed by the emulsion layers of the same spectral sensitivity. The digital record formed by scanning the dye image formed by an emulsion layer of the highest speed is used to recreate the portion of the dye image to be viewed lying just above minimum density. At higher exposure levels second and, optionally, third electronic records can be formed by scanning spectrally differentiated dye images formed by the remaining emulsion layer or layers. These digital records contain less noise (lower granularity) and can be used in recreating the image to be viewed over exposure ranges above the threshold exposure level of the slower emulsion layers. This technique for lowering granularity is disclosed in greater detail by Sutton U.S. Pat. No. 5,314,794, the disclosure of which is here incorporated by reference.

Each layer unit of the color negative elements of the invention produces a dye image characteristic curve gamma of less than 1.5, which facilitates obtaining an exposure latitude of at least 2.7 log E. A minimum acceptable exposure latitude of a multicolor photographic element is that which allows accurately recording the most extreme whites (e.g., a bride's wedding gown) and the most extreme blacks (e.g., a bride groom's tuxedo) that are likely to arise in photographic use. An exposure latitude of 2.6 log E can just accommodate the typical bride and groom wedding scene. An exposure latitude of at least 3.0 log E is preferred, since this allows for a comfortable margin of error in exposure level selection by a photographer. Even larger exposure latitudes are specifically preferred, since the ability to obtain accurate image reproduction with larger exposure errors is realized. Whereas in color negative elements intended for printing, the visual attractiveness of the printed scene is often lost when gamma is exceptionally low, when color negative elements are scanned to create digital dye image records, contrast can be increased by adjustment of the electronic signal information. When the elements of the invention are scanned using a reflected beam, the beam travels through the layer units twice. This effectively doubles gamma ($\Delta D \div \Delta \log E$) by doubling changes in density ($\Delta D$). Thus, gamma's as low as 1.0 or even 0.6 are contemplated and exposure latitudes of up to about 5.0 log E or higher are feasible. Gammas of about 0.55 are preferred. Gammas of between about 0.4 and 0.5 are especially preferred.

Instead of employing dye-forming couplers, any of the conventional incorporated dye image generating compounds employed in multicolor imaging can be alternatively incorporated in the blue, green and red recording layer units. Dye images can be produced by the selective destruction, formation or physical removal of dyes as a function of exposure. For example, silver dye bleach processes are well known and commercially utilized for forming dye images by the selective destruction of incorporated image dyes. The silver dye bleach process is illustrated by *Research Disclosure* I, Section X. Dye image formers and modifiers, A. Silver dye bleach.

It is also well known that preformed image dyes can be incorporated in blue, green and red recording layer units, the dyes being chosen to be initially immobile, but capable of releasing the dye chromophore in a mobile moiety as a function of entering into a redox reaction with oxidized developing agent. These compounds are commonly referred to as redox dye releasers (RDR's). By washing out the released mobile dyes, a retained dye image is created that can be scanned. It is also possible to transfer the released mobile dyes to a receiver, where they are immobilized in a mordant layer. The image-bearing receiver can then be scanned. Initially the receiver is an integral part of the color negative element. When scanning is conducted with the receiver remaining an integral part of the element, the receiver typically contains a transparent support, the dye image bearing mordant layer just beneath the support, and a white reflective layer just beneath the mordant layer. Where the receiver is peeled from the color negative element to facilitate scanning of the dye image, the receiver support can be reflective, as is commonly the choice when the dye image is intended to be viewed, or transparent, which allows transmission scanning of the dye image. RDR's as well as dye image transfer systems in which they are incorporated are described in *Research Disclosure*, Vol. 151, November 1976, Item 15162.

It is also recognized that the dye image can be provided by compounds that are initially mobile, but are rendered immobile during imagewise development. Image transfer systems utilizing imaging dyes of this type have long been used in previously disclosed dye image transfer systems. These and other image transfer systems compatible with the practice of the invention are disclosed in *Research Disclosure*, Vol. 176, December 1978, Item 17643, XXIII. Image transfer systems.

A number of modifications of color negative elements have been suggested for accommodating scanning, as illustrated by *Research Disclosure* I, Section XIV. Scan facilitating features. These systems to the extent compatible with the color negative element constructions described above are contemplated for use in the practice of this invention.

It is also contemplated that the imaging element of this invention may be used with non-conventional sensitization schemes. For example, instead of using imaging layers sensitized to the red, green, and blue regions of the spectrum, the light-sensitive material may have one white-sensitive layer to record scene luminance, and two color-sensitive layers-to record scene chrominance. Following development, the resulting image can be scanned and digitally reprocessed to reconstruct the full colors of the original scene as described in U.S. Pat. No. 5,962,205. The imaging element may also comprise a pan-sensitized emulsion with accompanying color-separation exposure. In this embodiment, the developers of the invention would give rise to a colored or neutral image which, in conjunction with the separation exposure, would enable full recovery of the original scene color values. In such an element, the image may be formed by either developed silver density, a combination of one or more conventional couplers, or "black" couplers such as resorcinol couplers. The separation exposure may be made either sequentially through appropriate filters, or simultaneously through a system of spatially discreet filter elements (commonly called a "color filter array").

The imaging element of the invention may also be a black and white image-forming material comprised, for example, of a pan-sensitized silver halide emulsion and a developer of the invention. In this embodiment, the image may be formed by developed silver density following processing, or by a coupler that generates a dye which can be used to carry the neutral image tone scale.

When conventional yellow, magenta, and cyan image dyes are formed to read out the recorded scene exposures following chemical development of conventional exposed color photographic materials, the response of the red, green, and blue color recording units of the element can be accurately discerned by examining their densities. Densitometry is the measurement of transmitted light by a sample using selected colored filters to separate the imagewise response of the RGB image dye forming units into relatively independent channels. It is common to use Status M filters to gauge the response of color negative film elements intended for optical printing, and Status A filters for color reversal films intended for direct transmission viewing. In integral densitometry, the unwanted side and tail absorptions of the imperfect image dyes leads to a small amount of channel mixing, where part of the total response of, for example, a magenta channel may come from. off-peak absorptions of either the yellow or cyan image dyes records, or both, in neutral characteristic curves. Such artifacts may be negligible in the measurement of a film's spectral sensitivity. By appropriate mathematical treatment of the integral density response, these unwanted off-peak density contributions can be completely corrected providing analytical densities, where the response of a given color record is independent of the spectral contributions of the other image dyes. Analytical density determination has been summarized in the *SPSE Handbook of Photographic Science and Engineering*, W. Thomas, editor, John Wiley and Sons, New York, 1973, Section 15.3, Color Densitometry, pp. 840-848.

Image noise can be reduced, where the images are obtained by scanning exposed and processed color negative film elements to obtain a manipulatable electronic record of the image pattern, followed by reconversion of the adjusted electronic record to a viewable form. Image sharpness and colorfulness can be increased by designing layer gamma ratios to be within a narrow range while avoiding or minimizing other performance deficiencies, where the color record is placed in an electronic form prior to recreating a color image to be viewed. Whereas it is impossible to separate image noise from the remainder of the image information, either in printing or by manipulating an electronic image record, it is possible by adjusting an electronic image record that exhibits low noise, as is provided by color negative film elements with low gamma ratios, to improve overall curve shape and sharpness characteristics in a manner that is impossible to achieve by known printing techniques. Thus, images can be recreated from electronic image records derived from such color negative elements that are superior to those similarly derived from conventional color negative elements constructed to serve optical printing applications. The excellent imaging characteristics of the described element are obtained when the gamma ratio for each of the red, green and blue color recording units is less than 1.2. In a more preferred embodiment, the red, green, and blue light sensitive color forming units each exhibit gamma ratios of less than 1.15. In an even more preferred embodiment, the red and blue light sensitive color forming units each exhibit gamma ratios of less than 1.10. In a most preferred embodiment, the red, green, and blue light sensitive color forming units each exhibit gamma ratios of less than 1.10. In all cases, it is preferred that the individual color unit(s) exhibit gamma ratios of less than 1.15, more preferred that they exhibit gamma ratios of less than 1.10 and even more preferred that they exhibit gamma ratios of less than 1.05. The gamma ratios of the layer units need not be equal. These low values of the gamma ratio are indicative of low levels of interlayer interaction, also known as interlayer interimage effects, between the layer units and are believed to account for the improved quality of the images after scanning and electronic manipulation. The apparently deleterious image characteristics that result from chemical interactions between the layer units need not be electronically suppressed during the image manipulation activity. The interactions are often difficult if not impossible to suppress properly using known electronic image manipulation schemes.

Elements having excellent light sensitivity are best employed in the practice of this invention. The elements should have a sensitivity of at least about ISO 50, preferably have a sensitivity of at least about ISO 100, and more preferably have a sensitivity of at least about ISO 200. Elements having a sensitivity of up to ISO 3200 or even higher are specifically contemplated. The speed, or sensitivity, of a color negative photographic element is inversely related to the exposure required to enable the attainment of a specified density above fog after processing. Photographic speed for a color negative element with a gamma of about 0.65 in each color record has been specifically defined by the American National Standards Institute (ANSI) as ANSI Standard Number PH 2.27-1981 (ISO (ASA Speed)) and relates specifically the average of exposure levels required to produce a density of 0.15 above the minimum density in each of the green light sensitive and least sensitive color recording unit of a color film. This definition conforms to the International Standards Organization (ISO) film speed rating. For the purposes of this application, if the color unit gammas differ from 0.65, the ASA or ISO speed is to be calculated by linearly amplifying or deamplifying the gamma vs. log E (exposure) curve to a value of 0.65 before determining the speed in the otherwise defined manner.

The present invention also contemplates the use of photographic elements of the present invention in what are often referred to as single use cameras (or "film with lens" units). These cameras are sold with film preloaded in them and the entire camera is returned to a processor with the exposed film remaining inside the camera. The one-time-use cameras employed in this invention can be any of those known in the art. These cameras can provide specific features as known in the art such as shutter means, film winding means, film advance means, waterproof housings, single or multiple lenses, lens selection means, variable aperture, focus or focal length lenses, means for monitoring lighting conditions, means for adjusting shutter times or lens characteristics based on lighting conditions or user provided instructions, and means for camera recording use conditions directly on the film. These features include, but are not limited to: providing simplified mechanisms for manually or automatically advancing film and resetting shutters as described at Skarman, U.S. Pat. No. 4,226,517; providing apparatus for automatic exposure control as described at Matterson et al, U.S. Pat. No. 4,345,835; moisture-proofing as described at Fujimura et al, U.S. Pat. No. 4,766,451; providing internal and external film casings as described at Ohmura et al, U.S. Pat. No. 4,751,536; providing means for recording use conditions on the film as described at Taniguchi et al, U.S. Pat. No. 4,780,735; providing lens fitted cameras as described at Arai, U.S. Pat. No. 4,804,987; providing film supports with superior anti-curl properties as described at Sasaki et al, U.S. Pat. No. 4,827,298; providing a viewfinder as described at Ohmura et al, U.S. Pat. No. 4,812,863; providing a lens of defined focal length and lens speed as described at Ushiro et al, U.S. Pat. No. 4,812,866; providing multiple film containers as described at Nakayama et al, U.S. Pat. No. 4,831,398 and at Ohmura et al, U.S. Pat. No. 4,833,495; providing films with improved anti-friction characteristics as described at Shiba, U.S. Pat. No. 4,866,469; providing winding mechanisms, rotating spools, or resilient sleeves as described at Mochida, U.S. Pat. No. 4,884,087; providing a film patrone or cartridge removable in an axial direction as described by Takei et al at U.S. Pat. Nos. 4,890,130 and 5,063,400; providing an electronic flash means as described at Ohmura et al, U.S. Pat. No. 4,896,178; providing an externally operable member for effecting exposure as described at Mochida et al, U.S. Pat. No. 4,954,857; providing film support with modified sprocket holes and means for advancing said film as described at Murakami, U.S. Pat. No. 5,049,908; providing internal mirrors as described at Hara, U.S. Pat. No. 5,084,719; and providing silver halide emulsions suitable for use on tightly wound spools as described at Yagi et al, European Patent Application 0,466,417 A.

While the film may be mounted in the one-time-use camera in any manner known in the art, it is especially preferred to mount the film in the one-time-use camera such that it is taken up on exposure by a thrust cartridge. Thrust cartridges are disclosed by Kataoka et al U.S. Pat. No. 5,226,613; by Zander U.S. Pat. No. 5,200,777; by Dowling et al U.S. Pat. No. 5,031,852; and by Robertson et al U.S. Pat. No. 4,834,306. Narrow bodied one-time-use cameras suitable for employing thrust cartridges in this way are described by Tobioka et al U.S. Pat. No. 5,692,221.

Cameras may contain a built-in processing capability, for example a heating element. Designs for such cameras including their use in an image capture and display system are disclosed in U.S. patent application Ser. No. 09/388,573 filed Sep. 1, 1999, incorporated herein by reference. The use of a one-time use camera as disclosed in said application is particularly preferred in the practice of this invention.

Photographic elements of the present invention are preferably imagewise exposed using any of the known techniques, including those described in *Research Disclosure* I, Section XVI. This typically involves exposure to light in the visible region of the spectrum, and typically such exposure is of a live image through a lens, although exposure can also be exposure to a stored image (such as a computer stored image) by means. of light emitting devices (such as light emitting diodes, CRT and the like). The photothermographic elements are also exposed by means of various forms of energy, including ultraviolet and infrared regions of the electromagnetic spectrum as well as electron beam and beta radiation, gamma ray, x-ray, alpha particle, neutron radiation and other forms of corpuscular wave-like radiant energy in either non-coherent (random phase) or coherent (in phase) forms produced by lasers. Exposures are monochromatic, orthochromatic, or panchromatic depending upon the spectral sensitization of the photographic silver halide.

The elements as discussed above may serve as origination material for some or all of the following processes: image scanning to produce an electronic rendition of the capture image, and subsequent digital processing of that rendition to manipulate, store, transmit, output, or display electronically that image.

The blocked compounds of this invention may be used in photographic elements that contain any or all of the features discussed above, but are intended for different forms of processing. These types of systems will be described in detail below.

Type I: Thermal process systems (thermographic and photothermographic), where processing is initiated solely by the application of heat to the imaging element.

Type II: Low volume systems, where film processing is initiated by contact to a processing solution, but where the processing solution volume is comparable to the total volume of the imaging layer to be processed. This type of system may include the addition of non solution processing aids, such as the application of heat or of a laminate layer that is applied at the time of processing.

Type III: Conventional photographic systems, where film elements are processed by contact with conventional photographic processing solutions, and the volume of such solutions is very large in comparison to the volume of the imaging layer.

Types I, II and III will now be discussed.

Type I: Thermographic and Photothermographic Systems

In accordance with one aspect of this invention the blocked developer is incorporated in a photothermographic element. Photothermographic elements of the type described in *Research Disclosure* 17029 are included by reference. The photothermographic elements may be of type A or type B as disclosed in *Research Disclosure* I. Type A elements contain in reactive association a photosensitive silver halide, a reducing agent or developer, an activator, and a coating vehicle or binder. In these systems development occurs by reduction of silver ions in the photosensitive silver halide to metallic silver. Type B systems can contain all of the elements of a type A system in addition to a salt or complex of an organic compound with silver ion. In these systems, this organic complex is reduced during development to yield silver metal. The organic silver salt will be referred to as the silver donor. References describing such imaging elements include, for example, U.S. Pat. Nos. 3,457,075; 4,459,350; 4,264,725 and 4,741,992.

The photothermographic element comprises a photosensitive component that consists essentially of photographic silver halide. In the type B photothermographic material it is believed that the latent image silver from the silver halide acts as a catalyst for the described image-forming combination upon processing. In these systems, a preferred concentration of photographic silver halide is within the range of 0.01 to 100 moles of photographic silver halide per mole of silver donor in the photothermographic material.

The Type B photothermographic element comprises an oxidation-reduction image forming combination that contains an organic silver salt oxidizing agent. The organic silver salt is a silver salt which is comparatively stable to light, but aids in the formation of a silver image when heated to 80° C. or higher in the presence of an exposed photocatalyst (i.e., the photosensitive silver halide) and a reducing agent.

Suitable organic silver salts include silver salts of organic compounds having a carboxyl group. Preferred examples thereof include a silver salt of an aliphatic carboxylic acid and a silver salt of an aromatic carboxylic acid. Preferred examples of the silver salts of aliphatic carboxylic acids include silver behenate, silver stearate, silver oleate, silver laureate, silver caprate, silver myristate, silver palmitate, silver maleate, silver fumarate, silver tartarate, silver furoate, silver linoleate, silver butyrate and silver camphorate, mixtures thereof, etc. Silver salts which are substitutable with a halogen atom or a hydroxyl group can also be effectively used. Preferred examples of the silver salts of aromatic carboxylic acid and other carboxyl group-containing compounds include silver benzoate, a silver-substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc., silver gallate, silver tannate, silver phthalate, silver terephthalate, silver salicylate, silver phenylacetate, silver pyromellilate, a silver salt of 3-carboxymethyl-4-methyl-4-thiazoline-2-thione or the like as described in U.S. Pat. No. 3,785,830, and silver salt of an aliphatic carboxylic acid containing a thioether group as described in U.S. Pat. No. 3,330,663.

Silver salts of mercapto or thione substituted compounds having a heterocyclic nucleus containing 5 or 6 ring atoms, at least one of which is nitrogen, with other ring atoms including carbon and up to two hetero-atoms selected from among oxygen, sulfur and nitrogen are specifically contemplated. Typical preferred heterocyclic nuclei include triazole, oxazole, thiazole, thiazoline, imidazoline, imidazole, diazole, pyridine and triazine. Preferred examples of these heterocyclic compounds include a silver salt of 3-mercapto-4-phenyl-1,2,4 triazole, a silver salt of 2-mercaptobenzimidazole, a silver salt of 2-mercapto-5-aminothiadiazole, a silver salt of 2-(2-ethyl-glycolamido)benzothiazole, a silver salt of 5-carboxylic-1-methyl-2-phenyl-4-thiopyridine a silver salt of mercaptotriazine, a silver salt of 2-mercaptobenzoxazole, a silver salt as described in U.S. Pat. No. 4,123,274, for example, a silver salt of 1,2,4-mercaptothiazole derivative such as a silver salt of 3-amino-5-benzylthio-1,2,4-thiazole, a silver salt of a thione compound such as a silver salt of 3-(2-carboxyethyl)-4-methyl-4-thiazoline-2-thione as disclosed in U.S. Pat. No. 3,201,678. Examples of other useful mercapto or thione substituted compounds that do not contain a heterocyclic nucleus are illustrated by the following: a silver salt of thioglycolic acid such as a silver salt of a S-alkylthioglycolic acid (wherein the alkyl group has from 12 to 22 carbon atoms) as described in Japanese patent application 28221/73, a silver salt of a dithiocarboxylic acid such as a silver salt of dithioacetic acid, and a silver salt of thioamide.

Furthermore, a silver salt of a compound containing an imino group can be used. Preferred examples of these compounds include a silver salt of benzotriazole and a derivative thereof as described in Japanese patent publications 30270/69 and 18146/70, for example a silver salt of benzotriazole or methylbenzotriazole, etc., a silver salt of a halogen substituted benzotriazole, such as a silver salt of 5-chlorobenzotriazole, etc., a silver salt of 1,2,4-triazole, a silver salt of 3-amino-5-mercaptobenzyl-1,2,4-triazole, of 1H-tetrazole as described in U.S. Pat. No. 4,220,709, a silver salt of imidazole and an imidazole derivative, and the like.

It is also found convenient to use silver half soap, of which an equimolar blend of a silver behenate with behenic acid, prepared by precipitation from aqueous solution of the sodium salt of commercial behenic acid and analyzing about 14.5 percent silver, represents a preferred example. Transparent sheet materials made on transparent film backing require a transparent coating and for this purpose the silver behenate full soap, containing not more than about 4 or 5 percent of free behenic acid and analyzing about 25.2 percent silver may be used. A method for making silver soap dispersions is well known in the art and is disclosed in *Research Disclosure* October 1983 (23419) and U.S. Pat. No. 3,985,565.

Silver salts complexes may also be prepared by mixture of aqueous solutions of a silver ionic species, such as silver nitrate, and a solution of the organic ligand to be complexed with silver. The mixture process may take any convenient form, including those employed in the process of silver halide precipitation. A stabilizer may be used to avoid flocculation of the silver complex particles. The stabilizer may be any of those materials known to be useful in the photographic art, such as, but not limited to, gelatin, polyvinyl alcohol or polymeric or monomeric surfactants.

The photosensitive silver halide grains and the organic silver salt are coated so that they are in catalytic proximity during development. They can be coated in contiguous layers, but are preferably mixed prior to coating. Conventional mixing techniques are illustrated by *Research Disclosure*, Item 17029, cited above, as well as U.S. Pat. No. 3,700,458 and published Japanese patent applications Nos. 32928/75, 13224/74, 17216/75 and 42729/76.

A reducing agent in addition to the blocked developer may be included. The reducing agent for the organic silver salt may be any material, preferably organic material, that can reduce silver ion to metallic silver. Conventional photographic developers such as 3-pyrazolidinones, hydroquinones, p-aminophenols, p-phenylenediamines and catechol are useful, but hindered phenol reducing agents are preferred. The reducing agent is preferably present in a concentration ranging from 5 to 25 percent of the photothermographic layer.

A wide range of reducing agents has been disclosed in dry silver systems including amidoximes such as phenylamidoxime, 2-thienylamidoxime and p-phenoxy-phenylamidoxime, azines (e.g., 4-hydroxy-3,5-dimethoxybenzaldehydeazine); a combination of aliphatic carboxylic acid aryl hydrazides and ascorbic acid, such as 2,2'-bis(hydroxymethyl)propionylbetaphenyl hydrazide in combination with ascorbic acid; an combination of polyhydroxybenzene and hydroxylamine, a reductone and/or a hydrazine, e.g., a combination of hydroquinone and bis(ethoxyethyl)hydroxylamine, piperidinohexose reductone or formyl-4-methylphenylhydrazine, hydroxamic acids such as phenylhydroxamic acid, p-hydroxyphenyl-hydroxamic acid, and o-alaninehydroxamic acid; a combination of azines and sulfonamidophenols, e.g., phenothiazine and 2,6-dichloro-4-benzenesulfonamidophenol; α-cyano-phenylacetic acid derivatives such as ethyl α-cyano-2-methylphenylacetate, ethyl α-cyano-phenylacetate; bis-β-naphthols as illustrated by 2,2'-dihydroxyl-1-binaphthyl, 6,6'-dibromo-2,2'-dihydroxy-1,1'-binaphthyl, and bis(2-hydroxy-1-naphthyl)methane; a combination of bis-o-naphthol and a 1,3-dihydroxybenzene derivative, (e. g., 2,4-dihydroxybenzophenone or 2,4-dihydroxyacetophenone); 5-pyrazolones such as 3-methyl-1-phenyl-5-pyrazolone; reductones as illustrated by dimethylaminohexose reductone, anhydrodihydroaminohexose reductone, and anhydrodihydro-piperidone-hexose reductone; sulfamidophenol reducing agents such as 2,6-dichloro-4-benzenesulfon-amido-phenol, and p-benzenesulfonamidophenol; 2-phenylindane-1,3-dione and the like; chromans such as 2,2-dimethyl-7-t-butyl-6-hydroxychroman; 1,4-dihydropyridines such as 2,6-dimethoxy-3,5-dicarbethoxy-1,4-dihydropyridene; bisphenols, e.g., bis(2-hydroxy-3-t-butyl-5-methylphenyl)-methane; 2,2-bis(4-hydroxy-3-methylphenyl)-propane; 4,4-ethylidene-bis(2-t-butyl-6-methylphenol); and 2,2-bis(3,5-dimethyl-4-hydroxyphenyl)propane; ascorbic acid derivatives, e.g., 1-ascorbyl-palnitate, ascorbylstearate and unsaturated aldehydes and ketones, such as benzyl and diacetyl; pyrazolidin-3-ones; and certain indane-1,3-diones.

An optimum concentration of organic reducing agent in the photothermographic element varies depending upon such factors as the particular photothermographic element, desired image, processing conditions, the particular organic silver salt and the particular oxidizing agent.

The photothermographic element can comprise a toning agent, also known as an activator-toner or toner-accelerator. (These may also function as thermal solvents or meltformers.) Combinations of toning agents are also useful in the photothermographic element. Examples of useful toning agents and toning agent combinations are described in, for example, *Research Disclosure*, June 1978, Item No. 17029 and U.S. Pat. No. 4,123,282. Examples of useful toning agents include, for example, salicylanilide, phthalimide, N-hydroxyphthalimide, N-potassium-phthalimide, succinimide, N-hydroxy-1,8-naphthalimide, phthalazine, 1-(2H)-phthalazinone, 2-acetylphthalazinone, benzanilide, and benzenesulfonamide. Prior-art thermal solvents are disclosed, for example, in U.S. Pat. No. 6,013,420 to Windender.

Post-processing image stabilizers and latent image keeping stabilizers are useful in the photothermographic element. Any of the stabilizers known in the photothermographic art are useful for the described photothermographic element. Illustrative examples of useful stabilizers include photolytically active stabilizers and stabilizer precursors as described in, for example, U.S. Pat. No. 4,459,350. Other examples of useful stabilizers include azole thioethers and blocked azolinethione stabilizer precursors and carbamoyl stabilizer precursors, such as described in U.S. Pat. No. 3,877,940.

The photothermographic elements preferably contain various colloids and polymers alone or in combination as vehicles and binders and in various layers. Useful materials are hydrophilic or hydrophobic. They are transparent or translucent and include both naturally occurring substances, such as gelatin, gelatin derivatives, cellulose derivatives, polysaccharides, such as dextran, gum arabic and the like; and synthetic polymeric substances, such as water-soluble polyvinyl compounds like poly(vinylpyrrolidone) and acrylamide polymers. Other synthetic polymeric compounds that are useful include dispersed vinyl compounds such as in latex form and particularly those that increase dimensional stability of photographic elements. Effective polymers include water insoluble polymers of acrylates, such as alkylacrylates and methacrylates, acrylic acid, sulfoacrylates, and those that have cross-linking sites. Preferred high molecular weight materials and resins include poly(vinyl butyral), cellulose acetate butyrate, poly(methylmethacrylate), poly(vinylpyrrolidone), ethyl cellulose, polystyrene, poly(vinylchloride), chlorinated rubbers, polyisobutylene, butadiene-styrene copolymers, copolymers of vinyl chloride and vinyl acetate, copolymers of vinylidene chloride and vinyl acetate, poly (vinyl alcohol) and polycarbonates. When coatings are made using organic solvents, organic soluble resins may be coated by direct mixture into the coating formulations. When coating from aqueous solution, any useful organic soluble materials may be incorporated as a latex or other fine particle dispersion.

Photothermographic elements as described can contain addenda that are known to aid in formation of a useful image. The photothermographic element can contain development modifiers that function as speed increasing compounds, sensitizing dyes, hardeners, antistatic agents, plasticizers and lubricants, coating aids, brighteners, absorbing and filter dyes, such as described in *Research Disclosure*, December 1978, Item No. 17643 and *Research Disclosure*, June 1978, Item No. 17029.

The layers of the photothermographic element are coated on a support by coating procedures known in the photographic art, including dip coating, air knife coating, curtain coating or extrusion coating using hoppers. If desired, two or more layers are coated simultaneously.

A photothermographic element as described preferably comprises a thermal stabilizer to help stabilize the photothermographic element prior to exposure and processing. Such a thermal stabilizer provides improved stability of the photothermographic element during storage. Preferred thermal stabilizers are 2-bromo-2-arylsulfonylacetamides, such as 2-bromo-2-p-tolysulfonylacetamide; 2-(tribromomethyl sulfonyl)benzothiazole; and 6-substituted-2,4-bis(tribromomethyl)-s-triazines, such as 6-methyl or 6-phenyl-2,4-bis(tribromomethyl)-s-triazine.

Imagewise exposure is preferably for a time and intensity sufficient to produce a developable latent image in the photothermographic element.

After imagewise exposure of the photothermographic element, the resulting latent image can be developed in a variety of ways. The simplest is by overall heating the element to thermal processing temperature. This overall heating merely involves heating the photothermographic element to a temperature within the range of about 90° C. to about 180° C. until a developed image is formed, such as within about 0.5 to about 60 seconds. By increasing or decreasing the thermal processing temperature a shorter or longer time of processing is useful. A preferred thermal processing temperature is within the range of about 100° C. to about 160° C. Heating means known in the photothermographic arts are useful for providing the desired processing temperature for the exposed photothermographic element. The heating means is, for example, a simple hot plate, iron, roller, heated drum, microwave heating means, heated air, vapor or the like.

It is contemplated that the design of the processor for the photothernographic element be linked to the design of the cassette or cartridge used for storage and use of the element. Further, data stored on the film or cartridge may be used to modify processing conditions or scanning of the element. Methods for accomplishing these steps in the imaging system are disclosed in commonly assigned, co-pending U.S. patent applications Ser. Nos. 09/206586, 09/206,612, and 09/206,583 filed Dec. 7, 1998, which are incorporated herein by reference. The use of an apparatus whereby the processor can be used to write information onto the element, information which can be used to adjust processing, scanning, and image display is also envisaged. This system is disclosed in U.S. patent applications Ser. Nos. 09/206,914 filed Dec. 7, 1998 and 09/333,092 filed Jun. 15, 1999, which are incorporated herein by reference.

Thermal processing is preferably carried out under ambient conditions of pressure and humidity. Conditions outside of normal atmospheric pressure and humidity are useful.

The components of the photothermographic element can be in any location in the element that provides the desired image. If desired, one or more of the components can be in one or more layers of the element. For example, in some cases, it is desirable to include certain percentages of the reducing agent, toner, stabilizer and/or other addenda in the overcoat layer over the photothermographic image recording layer of the element. This, in some cases, reduces migration of certain addenda in the layers of the element.

In accordance with one aspect of this invention the blocked developer is incorporated in a thermographic element. In thermographic elements an image is formed by imagewise heating the element. Such elements are described in, for example, *Research Disclosure*, June 1978, Item No. 17029 and U.S. Pat. Nos. 3,080,254, 3,457,075 and 3,933,508, the disclosures or which are incorporated herein by reference. The thermal energy source and means for imaging can be any imagewise thermal exposure source and means that are known in the thermographic imaging art. The thermographic imaging means can be, for example, an infrared heating means, laser, microwave heating means or the like.

Type II: Low Volume Processing

In accordance with another aspect of this invention the blocked developer is incorporated in a photographic element intended for low volume processing. Low volume processing is defined as processing where the volume of applied developer solution is between about 0.1 to about 10 times, preferably about 0.5 to about 10 times, the volume of solution required to swell the photographic element. This processing may take place by a combination of solution application, external layer lamination, and heating. The low volume processing system may contain any of the elements described above for Type I: Photothermographic systems. In addition, it is specifically contemplated that any components described in the preceding sections that are not necessary for the formation or stability of latent image in the origination film element can be removed from the film element altogether and contacted at any time after exposure for the purpose of carrying out photographic processing, using the methods described below.

The Type II photographic element may receive some or all of the following treatments:

(I) Application of a solution directly to the film by any means, including spray, inkjet, coating, gravure process and the like.

(II) Soaking of the film in a reservoir containing a processing solution. This process may also take the form of dipping or passing an element through a small cartridge.

(III) Lamination of an auxiliary processing element to the imaging element. The laminate may have the purpose of providing processing chemistry, removing spent chemistry, or transferring image information from the latent image recording film element. The transferred image may result from a dye, dye precursor, or silver containing compound being transferred in a image-wise manner to the auxiliary processing element.

(IV) Heating of the element by any convenient means, including a simple hot plate, iron, roller, heated drum, microwave heating means, heated air, vapor, or the like. Heating may be accomplished before, during, after, or throughout any of the preceding treatments I-III. Heating may cause processing temperatures ranging from room temperature to 100° C.

Type III: Conventional Systems

In accordance with another aspect of this invention the blocked developer is incorporated in a conventional photographic element.

Conventional photographic elements in accordance with the invention can be processed in any of a number of well-known photographic processes utilizing any of a number of well-known conventional photographic processing solutions, described, for example, in *Research Disclosure* I, or in T. H. James, editor, *The Theory of the Photographic Process*, 4th Edition, Macmillan, New York, 1977. The development process may take place for any length of time and any process temperature that is suitable to render an acceptable image. In these cases the presence of blocked developers of the invention may be used to provide development in one or more color records of the element, supplementary to the development provided by the developer in the processing solution to give improved signal in a shorter time of development or with lowered laydowns of imaging materials, or to give balanced development in all color records. In the case of processing a negative working element, the element is treated with a color developer (that is one which will form the colored image dyes with the color couplers), and then with a oxidizer and a solvent to remove silver and silver halide. In the case of processing a reversal color element, the element is first treated with a black and white developer (that is, a developer which does not form colored dyes with the coupler compounds) followed by a treatment to fog silver halide (usually chemical fogging or light fogging), followed by treatment with a color developer. Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N-(2-(methanesulfonamido) ethylaniline sesquisulfate hydrate, 4-amino-3-methyl-N-ethyl-N-(2-hydroxyethyl) aniline sulfate, 4-amino-3-α-(methanesulfonamido)ethyl-N,N-diethylaniline hydrochloride and 4-amino-N-ethyl-N-(2-methoxyethyl)-m-toluidine di-p-toluene sulfonic acid.

Dye images can be formed or amplified by processes which employ in combination with a dye-image-generating reducing agent an inert transition metal-ion complex oxidizing agent, as illustrated by Bissonette U.S. Pat. Nos. 3,748,138, 3,826,652, 3,862,842 and 3,989,526 and Travis U.S. Pat. No. 3,765,891, and/or a peroxide oxidizing agent as illustrated by Matejec U.S. Pat. No. 3,674,490, *Research Disclosure*, Vol. 116, December, 1973, Item 11660, and Bissonette *Research Disclosure*, Vol. 148, August, 1976, Items 14836, 14846 and 14847. The photographic elements can be particularly adapted to form dye images by such processes as illustrated by Dunn et al U.S. Pat. No. 3,822,129, Bissonette U.S. Pat. Nos. 3,834,907 and 3,902,905, Bissonette et al U.S. Pat. No. 3,847,619, Mowrey U.S. Pat. No. 3,904,413, Hirai et al U.S. Pat. No. 4,880,725, Iwano U.S. Pat. No. 4,954,425, Marsden et al U.S. Pat. No. 4,983,504, Evans et al U.S. Pat. No. 5,246,822, Twist U.S. Pat. No. 5,324,624, Fyson EPO 0 487 616, Tannahill et al WO 90/13059, Marsden et al WO 90/13061, Grimsey et al WO 91/16666, Fyson WO 91/17479, Marsden et al WO 92/01972. Tannahill WO 92/05471, Henson WO 92/07299, Twist WO 93/01524 and WO 93/11460 and Wingender et al German OLS 4,211,460.

Development may be followed by bleach-fixing, to remove silver or silver halide, washing and drying.

Once yellow, magenta, and cyan dye image records have been formed in the processed photographic elements of the invention, conventional techniques can be employed for retrieving the image information for each color record and manipulating the record for subsequent creation of a color balanced viewable image. For example, it is possible to scan the photographic element successively within the blue, green, and red regions of the spectrum or to incorporate blue, green, and red light within a single scanning beam that is divided and passed through blue, green, and red filters to form separate scanning beams for each color record. A simple technique is to scan the photographic element point-by-point along a series of laterally offset parallel scan paths. The intensity of light passing through the element at a scanning point is noted by a sensor which converts radiation received into an electrical signal. Most generally this electronic signal is further manipulated to form a useful electronic record of the image. For example, the electrical signal can be passed through an analog-to-digital converter and sent to a digital computer together with location information required for pixel (point) location within the image. In another embodiment, this electronic signal is encoded with colorimetric or tonal information to form an electronic record that is suitable to allow reconstruction of the image into viewable forms such as computer monitor displayed images, television images, printed images, and so forth.

It is contemplated that many of imaging elements of this invention will be scanned prior to the removal of silver halide from the element. The remaining silver halide yields a turbid coating, and it is found that improved scanned image quality for such a system can be obtained by the use of scanners that employ diffuse illumination optics. Any technique known in the art for producing diffuse illumination can be used. Preferred systems include reflective systems, that employ a diffusing cavity whose interior walls are specifically designed to produce a high degree of diffuse reflection, and transmissive systems, where diffusion of a beam of specular light is accomplished by the use of an optical element placed in the beam that serves to scatter light. Such elements can be either glass or plastic that either incorporate a component that produces the desired scattering, or have been given a surface treatment to promote the desired scattering.

One of the challenges encountered in producing images from information extracted by scanning is that the number of pixels of information available for viewing is only a fraction of that available from a comparable classical photographic print. It is, therefore, even more important in scan imaging to maximize the quality of the image information available. Enhancing image sharpness and minimizing the impact of aberrant pixel signals (i.e., noise) are common approaches to enhancing image quality. A conventional technique for minimizing the impact of aberrant pixel signals is to adjust each pixel density reading to a weighted average value by factoring in readings from adjacent pixels, closer adjacent pixels being weighted more heavily.

The elements of the invention can have density calibration patches derived from one or more patch areas on a portion of unexposed photographic recording material that was subjected to reference exposures, as described by Wheeler et al U.S. Pat. No. 5,649,260, Koeng at al U.S. Pat. No. 5,563,717, and by Cosgrove et al U.S. Pat. No. 5,644,647.

Illustrative systems of scan signal manipulation, including techniques for maximizing the quality of image records, are disclosed by Bayer U.S. Pat. No. 4,553,156; Urabe et al U.S. Pat. No. 4,591,923; Sasaki et al U.S. Pat. No. 4,631,578; Alkofer U.S. Pat. No. 4,654,722; Yamada et al U.S. Pat. No. 4,670,793; Klees U.S. Pat. Nos. 4,694,342 and 4,962,542; Powell U.S. Pat. No. 4,805,031; Mayne et al U.S. Pat. No. 4,829,370; Abdulwahab U.S. Pat. No. 4,839,721; Matsunawa et al U.S. Pat. Nos. 4,841,361 and 4,937,662; Mizukoshi et al U.S. Pat. No. 4,891,713; Petilli U.S. Pat. No. 4,912,569; Sullivan et al U.S. Pat. Nos. 4,920,501 and 5,070,413; Kimoto et al U.S. Pat. No. 4,929,979; Hirosawa et al U.S. Pat. No. 4,972,256; Kaplan U.S. Pat. No. 4,977,521; Sakai U.S. Pat. No. 4,979,027; Ng U.S. Pat. No. 5,003,494; Katayama et al U.S. Pat. No. 5,008,950; Kimura et al U.S. Pat. No. 5,065, 255; Osamu et al U.S. Pat. No. 5,051,842; Lee et al U.S. Pat. No. 5,012,333; Bowers et al U.S. Pat. No. 5,107,346; Telle U.S. Pat. No. 5,105,266; MacDonald et al U.S. Pat. No. 5,105,469; and Kwon et al U.S. Pat. No. 5,081,692. Techniques for color balance adjustments during scanning are disclosed by Moore et al U.S. Pat. No. 5,049,984 and Davis U.S. Pat. No. 5,541,645.

The digital color records once acquired are in most instances adjusted to produce a pleasingly color balanced image for viewing and to preserve the color fidelity of the image bearing signals through various transformations or renderings for outputting, either on a video monitor or when printed as a conventional color print. Preferred techniques for transforming image bearing signals after scanning are disclosed by Giorgianni et al U.S. Pat. No. 5,267,030, the disclosures of which are herein incorporated by reference. Further illustrations of the capability of those skilled in the art to manage color digital image information are provided by Giorgianni and Madden *Digital Color Management*, Addison-Wesley, 1998.

FIG. 1 shows, in block diagram form, the manner in which the image information provided by the color negative elements of the invention is contemplated to be used. An image scanner 2 is used to scan by transmission an imagewise exposed and photographically processed color negative element 1 according to the invention. The scanning beam is most conveniently a beam of white light that is split after passage through the layer units and passed through filters to create separate image records-red recording layer unit image record (R), green recording layer unit image record (G), and blue recording layer unit image record (B). Instead of splitting the beam, blue, green, and red filters can be sequentially caused to intersect the beam at each pixel location. In still another scanning variation, separate blue, green, and red light beams, as produced by a collection of light emitting diodes, can be directed at each pixel location. As the element 1 is scanned pixel-by-pixel using an array detector, such as an array charge-coupled device (CCD), or line-by-line using a linear array detector, such as a linear array CCD, a sequence of R, G, and B picture element signals are generated that can be correlated with spatial location information provided from the scanner. Signal intensity and location information is fed to a workstation 4, and the information is transformed into an electronic form R', G', and B', which can be stored in any convenient storage device 5.

In motion imaging industries, a common approach is to transfer the color negative film information into a video signal using a telecine transfer device. Two types of telecine transfer devices are most common: (1) a flying spot scanner using photomultiplier tube detectors or (2) CCD's as sensors. These devices transform the scanning beam that has passed through the color negative film at each pixel location into a voltage. The signal processing then inverts the electrical signal in order to render a positive image. The signal is then amplified and modulated and fed into a cathode ray tube monitor to display the image or recorded onto magnetic tape for storage. Although both analog and digital image signal manipulations are contemplated, it is preferred to place the signal in a digital form for manipulation, since the overwhelming majority of computers are now digital and this facilitates use with common computer peripherals, such as magnetic tape, a magnetic disk, or an optical disk.

A video monitor 6, which receives the digital image information modified for its requirements, indicated by R", G", and B", allows viewing of the image information received by the workstation. Instead of relying on a cathode ray tube of a video monitor, a liquid crystal display panel or any other convenient electronic image viewing device can be substituted. The video monitor typically relies upon a picture control apparatus 3, which can include a keyboard and cursor, enabling the workstation operator to provide image manipulation commands for modifying the video image displayed and any image to be recreated from the digital image information.

Any modifications of the image can be viewed as they are being introduced on the video display 6 and stored in the storage device 5. The modified image information R'", G'", and B''' can be sent to an output device 7 to produce a recreated image for viewing. The output device can be any convenient conventional element writer, such as a thermal dye transfer, inkjet, electrostatic, electrophotographic, electrostatic, thermal dye sublimation or other type of printer. CRT or LED printing to sensitized photographic paper is also contemplated. The output device can be used to control the exposure of a conventional silver halide color paper. The output device creates an output medium 8 that bears the recreated image for viewing. It is the image in the output medium that is ultimately viewed and judged by the end user for noise (granularity), sharpness, contrast, and color balance. The image on a video display may also ultimately be viewed and judged by the end user for noise, sharpness, tone scale, color balance, and color reproduction, as in the case of images transmitted between parties on the World Wide Web of the Internet computer network.

Using an arrangement of the type shown in FIG. 1, the images contained in color negative elements in accordance with the invention are converted to digital form, manipulated, and recreated in a viewable form. Color negative recording materials according to the invention can be used with any of the suitable methods described in U.S. Pat. No. 5,257,030. In one preferred embodiment, Giorgianni et al provides for a method and means to convert the R, G, and B image-bearing signals from a transmission scanner to an image manipulation and/or storage metric which corresponds to the trichromatic signals of a reference image-producing device such as a film or paper writer, thermal printer, video display, etc. The metric values correspond to those which would be required to appropriately reproduce the color image on that device. For example, if the reference image producing device was chosen to be a specific video display, and the intermediary image data metric was chosen to be the R', G', and B' intensity modulating signals (code values) for that reference video display, then for an input film, the R, G, and B image-bearing signals from a scanner would be transformed to the R', G', and B' code values corresponding to those which would be required to appropriately reproduce the input image on the reference video display. A data-set is generated from which the mathematical transformations to convert R, G, and B image-bearing signals to the aforementioned code values are derived. Exposure patterns, chosen to adequately sample and cover the useful exposure range of the film being calibrated, are created by exposing a pattern generator and are fed to an exposing apparatus. The exposing apparatus produces trichromatic exposures on film to create test images consisting of approximately 150 color patches. Test images may be created using a variety of methods appropriate for the application. These methods include: using exposing apparatus such as a sensitometer, using the output device of a color imaging apparatus, recording images of test objects of known reflectances illuminated by known light sources, or calculating trichromatic exposure values using methods known in the photographic art. If input films of different speeds are used, the overall red, green, and blue exposures must be properly adjusted for each film in order to compensate for the relative speed differences among the films. Each film thus receives equivalent exposures, appropriate for its red, green, and blue speeds. The exposed film is processed chemically. Film color patches are read by transmission scanner which produces R, G, and B image-bearing signals corresponding each color patch. Signal-value patterns of code value pattern generator produces RGB intensity-modulating signals which are fed to the reference video display. The R', G', and B' code values for each test color are adjusted such that a color matching apparatus, which may correspond to an instrument or a human observer, indicates that the video display test colors match the positive film test colors or the colors of a printed negative. A transform apparatus creates a transform relating the R, G, and B image-bearing signal values for the film's test colors to the R', G', and B' code values of the corresponding test colors.

The mathematical operations required to transform R, G, and B image-bearing signals to the intermediary data may consist of a sequence of matrix operations and look-up tables (LUT's).

Figure 2:
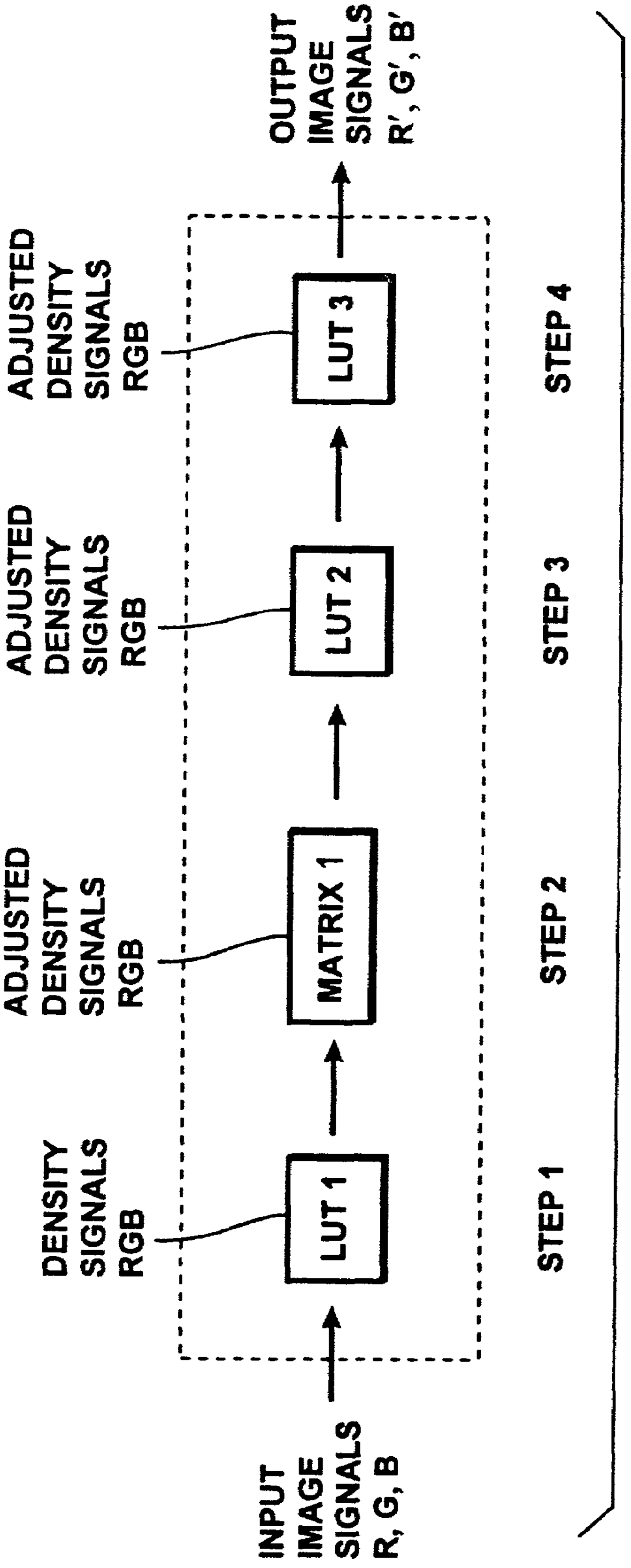
FIG. 2 shows a block diagram showing electronic signal processing of image bearing signals derived from scanning a developed color element according to the invention.

Referring to FIG. 2, in a preferred embodiment of the present invention, input image-bearing signals R, G, and B are transformed to intermediary data values corresponding to the R', G', and B' output image-bearing signals required to appropriately reproduce the color image on the reference output device as follows:

(1) The R, G, and B image-bearing signals, which correspond to the measured transmittances of the film, are converted to corresponding densities in the computer used to receive and store the signals from a film scanner by means of 1-dimensional look-up table LUT 1.

(2) The densities from step (1) are then transformed using matrix 1 derived from a transform apparatus to create intermediary image-bearing signals.

(3) The densities of step (2) are optionally modified with a 1-dimensional look-up table LUT 2 derived such that the neutral scale densities of the input film are transformed to the neutral scale densities of the reference.

(4) The densities of step (3) are transformed through a 1-dimensional look-up table LUT 3 to create corresponding R', G', and B' output image-bearing signals for the reference output device.

It will be understood that individual look-up tables are typically provided for each input color. In one embodiment, three 1-dimensional look-up tables can be employed, one for each of a red, green, and blue color record. In another embodiment, a multi-dimensional look-up table can be employed as described by D'Errico at U.S. Pat. No. 4,941,039. It will be appreciated that the output image-bearing signals for the reference output device of step 4 above may be in the form of device-dependent code values or the output image-bearing signals may require further adjustment to become device specific code values. Such adjustment may be accomplished by further matrix transformation or 1-dimensional look-up table transformation, or a combination of such transformations to properly prepare the output image-bearing signals for any of the steps of transmitting, storing, printing, or displaying them using the specified device.

In a second preferred embodiment of the invention, the R, G, and B image-bearing signals from a transmission scanner are converted to an image manipulation and/or storage metric which corresponds to a measurement or description of a single reference image-recording device and/or medium and in which the metric values for all input media correspond to the trichromatic values which would have been formed by the reference device or medium had it captured the original scene under the same conditions under which the input media captured that scene. For example, if the reference image recording medium was chosen to be a specific color negative film, and the intermediary image data metric was chosen to be the measured RGB densities of that reference film, then for an input color negative film according to the invention, the R, G, and B image-bearing signals from a scanner would be transformed to the R', G', and B' density values corresponding to those of an image which would have been formed by the reference color negative film had it been exposed under the same conditions under which the color negative recording material according to the invention was exposed.

Exposure patterns, chosen to adequately sample and cover the useful exposure range of the film being calibrated, are created by exposing a pattern generator and are fed to an exposing apparatus. The exposing apparatus produces trichromatic exposures on film to create test images consisting of approximately 150 color patches. Test images may be created using a variety of methods appropriate for the application. These methods include: using exposing apparatus such as a sensitometer, using the output device of a color imaging apparatus, recording images of test objects of known reflectances illuminated by known light sources, or calculating trichromatic exposure values using methods known in the photographic art. If input films of different speeds are used, the overall red, green, and blue exposures must be properly adjusted for each film in order to compensate for the relative speed differences among the films. Each film thus receives equivalent exposures, appropriate for its red, green, and blue speeds. The exposed film is processed chemically. Film color patches are read by a transmission scanner which produces R, G, and B image-bearing signals corresponding each color patch and by a transmission densitometer which produces R', G', and B' density values corresponding to each patch. A transform apparatus creates a transform relating the R, G, and B image-bearing signal values for the film's test colors to the measured R', G', and B' densities of the corresponding test colors of the reference color negative film. In another preferred variation, if the reference image recording medium was chosen to be a specific color negative film, and the intermediary image data metric was chosen to be the predetermined R', G', and B' intermediary densities of step 2 of that reference film, then for an input color negative film according to the invention, the R, G, and B image-bearing signals from a scanner would be transformed to the R', G', and B' intermediary density values corresponding to those of an image which would have been formed by the reference color negative film had it been exposed under the same conditions under which the color negative recording material according to the invention was exposed.

Thus, each input film calibrated according to the present method would yield, insofar as possible, identical intermediary data values corresponding to the R', G', and B' code values required to appropriately reproduce the color image which would have been formed by the reference color negative film on the reference output device. Uncalibrated films may also be used with transformations derived for similar types of films, and the results would be similar to those described.

The mathematical operations required to transform R, G, and B image-bearing signals to the intermediary data metric of this preferred embodiment may consist of a sequence of matrix operations and 1-dimensional LUTs. Three tables are typically provided for the three input colors. It is appreciated that such transformations can also be accomplished in other embodiments by employing a single mathematical operation or a combination of mathematical operations in the computational steps produced by the host computer including, but not limited to, matrix algebra, algebraic expressions dependent on one or more of the image-bearing signals, and n-dimensional LUTs. In one embodiment, matrix 1 of step 2 is a 3×3 matrix. In a more preferred embodiment, matrix 1 of step 2 is a 3×10 matrix. In a preferred embodiment, the 1-dimensional LUT 3 in step 4 transforms the intermediary image-bearing signals according to a color photographic paper characteristic curve, thereby reproducing normal color print image tone scale. In another preferred embodiment, LUT 3 of step 4 transforms the intermediary image-bearing signals according to a modified viewing tone scale that is more pleasing, such as possessing lower image contrast.

Due to the complexity of these transformations, it should be noted that the transformation from R, G, and B to R', G', and B' may often be better accomplished by a 3-dimensional LUT. Such 3-dimensional LUTs may be developed according to the teachings J. D'Errico in U.S. Pat. No. 4,941,039.

It is to be appreciated that while the images are in electronic form, the image processing is not limited to the specific manipulations described above. While the image is in this form, additional image manipulation may be used including, but not limited to, standard scene balance algorithms (to determine corrections for density and color balance based on the densities of one or more areas within the negative), tone scale manipulations to amplify film underexposure gamma, non-adaptive or adaptive sharpening via convolution or unsharp masking, red-eye reduction, and non-adaptive or adaptive grain-suppression. Moreover, the image may be artistically manipulated, zoomed, cropped, and combined with additional images or other manipulations known in the art. Once the image has been corrected and any additional image processing and manipulation has occurred, the image may be electronically transmitted to a remote location or locally written to a variety of output devices including, but not limited to, silver balide film or paper writers, thermal printers, electrophotographic printers, ink-jet printers, display monitors, CD disks, optical and magnetic electronic signal storage devices, and other types of storage and display devices as known in the art.

In yet another embodiment of the invention, the luminance and chrominance sensitization and image extraction article and method described by Arakawa et al in U.S. Pat. No. 5,962,205 can be employed. The disclosures of Arakawa et al are incorporated by reference.

EXAMPLE 1

This Example illustrates the Preparation of D-7 according to the following reaction scheme:

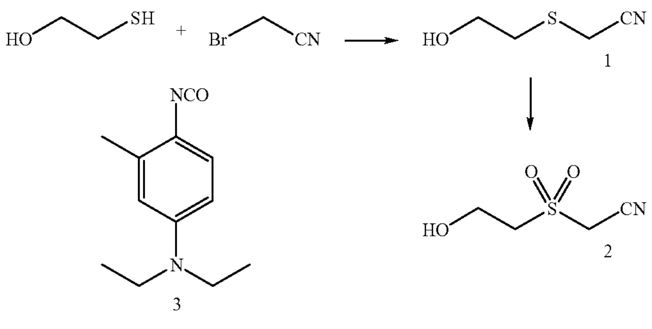

1

2

3

-continued

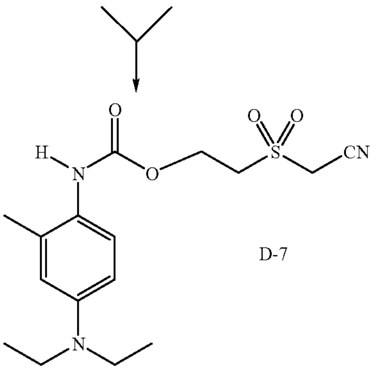

D-7

Preparation Of Intermediate 1:

A mixture of bromoacetonitrile (Aldrich, 12.00 g, 100 mmol), 2-mercaptoethanol (Fluka, 9.36 g, 120 mmol) and potassium carbonate (19.34 g, 140 mmol) in 200 mL of acetonitrile was stirred at room temperature for 22 h. The mixture was then filtered, the filtrate concentrated to an oil which was worked up with water and ethyl acetate, giving 6.73 g (57 mmol, 57%) of 1.

Preparation Of Intermediate 2:

A solution of 2 (6.73 g, 57 mmol) in 50 mL of ethanol was added to a suspension of tungstic acid (120 mg), that was neutralized with 2 drops of 50% aqueous sodium hydroxide, in 16 mL of water. The mixture was then treated with 12 mL of 30% hydrogen peroxide and refluxed for 1 h 15 min. Work-up with brine and ethyl acetate yielded 5.69 g of 2 (38 mmmol, 67%).

Preparation of D-7:

A solution of 2 (5.69 g, 38 mmol), compound 3 prepared as described in Brit. Pat. 1,152,877 (9.19 g, 45 mmol), and dibutyltin diacetate (0.02 mL) in acetonitrile (50 mL) was kept at room temperature in a stoppered flask for 4 days. The solvent was removed and the crude product purified by column chromatography (silica, ethyl acetate/heptane). Recrystallization from isopropyl ether produced 8.78 g of D-7 (25 mmol, 65%), m.p. 92-95° C., ESMS: $ES^+$, m/z 354 (M+1, base).

EXAMPLE 2

Blocked developer D-8 was prepared as described for D-7 in Example 1 above, beginning with 2-mercaptoethanol and ethyl bromoacetate. The yield of the final step was 4.98 g (12.4 mmmol, 36%), m.p. 62-63° C., ESMS: $ES^+$, m/z 401 (M+1, base).

EXAMPLE 3

This Example illustrates the preparation of blocked developer D-6, which was prepared according to the following reaction scheme:

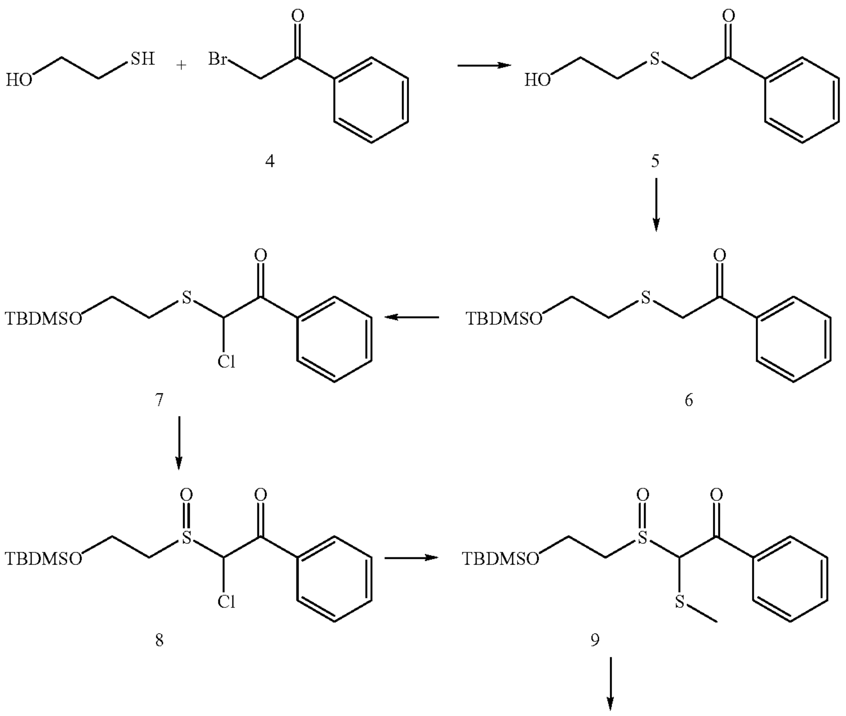

4 5 7 6 8 9

-continued

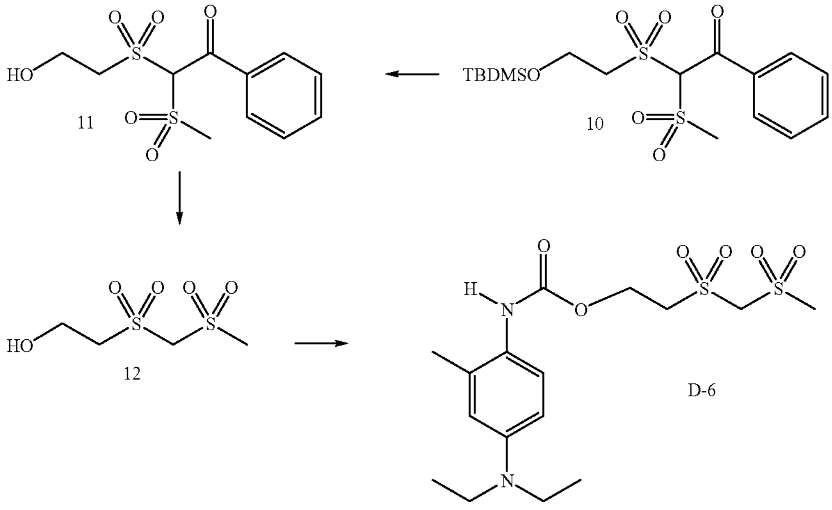

11 10 12 D-6

Preparation of Intermediate 5:

A solution of 2'-bromoacetophenone 4 (Aldrich, 19.91 g, 100 mmol) in 100 mL of acetonitrile was added in drops over a period of 30 min to a cooled (5° C.) solution of 2-mercaptoethanol (8.19 g, 105 mmol) in 100 mL of acetonitrile, containing potassium carbonate (15.20 g, 110 mmol). Following the addition the mixture was stirred at room temperature for 1 h and filtered. The filtrate was diluted with 200 mL of ether and washed with brine (50 mL). The ethereal solution was dried over sodium sulfate and concentrated in vacuo to give 19.96 g of 5 (100 mmol, 100%).

Preparation of Intermediate 6:

Solid tert-butyldimethylsilyl chloride (TBDMSC1, Aldrich, 18.09 g, 120 mmol) was added in one portion to a solution of 5 (19.96 g, 100 mmol) and imidazole (9.55 g, 140 mmol) in 250 mL of tetrahydrofuran, stirred under nitrogen. After 18 h at room temperature the mixture was quenched with 200 mL of saturated aqueous sodium bicarbonate and extracted with ether. The crude product was filtered through silica gel (ether/heptane) giving 31.60 g (100 mmol, 100%) of 6.

Preparation Of Intermediate 7:

Solid N-chlorosuccinimide (7.08 g, 53 mmol) was added in portions over a period of 30 min to a solution of 6 (16.23 g, 52.3 mmol) in 125 mL of carbon tetrachloride that was stirred at 5° C. The reaction was run for 2 h and filtered. Removal of the solvent left 18.70 g of 7 as an oil (52.3 mmol, 100%).

Preparation of Intermediate 8:

A solution of m-chloroperbenzoic acid (m-CPBA, Aldrich, 77%, 11.77 g, 52.3 mmol) in 100 mL of dichloromethane was added in drops over a period of 40 min to a solution of 7 (18.70 g, 52.3 mmol) in 100 mL of dichloromethane, stirred at −15° C. Following the addition, the mixture was stirred at −15° C. for 30 min and then at room temperature for 3 h. The reaction was quenched with saturated aqueous sodium bicarbonate (50 mL) and the organic layer was dried and concentrated. The crude product was purified by column chromatography (silica, heptane/dichloromethane) giving 15.56 g of 8 as an oil (43 mmol, 82%).

Preparation Of Intermediate 9:

Solid sodium thiomethoxide (Aldrich, 3.01 g, 43 mmol) was added in one portion to a solution of 8 (15.56 g, 43 mmol) in acetonitrile (150 mL) that was stirred at 5° C. The resulting mixture was stirred at 5° C. for 1 h and at room temperature for 2 h. Filtration and solvent removal from the filtrate produced and oil which crystallized (11.82 g). The solid that was collected by filtration was suspended in water, the mixture neutralized with acetic acid and extracted with ether. The extracts were concentrated in vacuo, the residue dissolved in acetonitrile (20 mL) and stirred with sodium thiomethoxide (0.42 g, 6 mmol) for 18 h, producing an additional 3.10 g of the product. Total yield of 9:14.92 g (40 mmol, 93%).

Preparation Of Intermediate 10:

Solid m-chloroperbenzoic acid (77%, 31.33 g, 139 mmol) was added in portions over a period of 45 min to a solution of 9 (14.82 g, 39.8 mmol) in 300 mL of dichloromethane that was stirred at −15° C. The reaction was run for 2 h at room temperature and quenched with saturated aqueous sodium bicarbonate (150 mL) and the organic layer was dried and concentrated. Purification by column chromatography (silica, dichloromethane/heptane) gave 12.88 g of solid 10 (30.6 mmol, 77%).

Preparation Of Intermediate 11:

Concentrated hydrochloric acid (0.5 mL) was added to a solution of 10 (8.29 g, 19.7 mmol) in methanol (100 mL)/dichloromethane (20 mL). The solution was stirred at room temperature for 24 h, the solvent distilled off and the solid residue washed with isopropyl ether and dried. The yield of 11 was 6.00 g (19.6 mmol, 99%).

Preparation Of Interinediate 12:

A solution of 11 (5.05 g, 16.5 mmol) in 100 mL of methanol, containing 0.25 mL of sulfuric acid, was refluxed for 2 weeks. The solvent was distilled off and the residue stirred with isopropyl ether giving a solid that was purified as its TBDMS derivative. The yield of 12 was 3.03 g (14.9 mmol, 91%).

Preparation Of D-6:

A solution of 12 (3.03 g, 14.9 mmol), compound 3 (3.06 g, 15 mmol) and dibutyltin diacetate (0.02 mL) in acetonitrile (50 mL) was kept at room temperature in a stoppered flask for 3 days. The solvent was removed giving a crystalline product which was washed with isopropyl ether and dried. The yield of D-7 was 5.80 g (14.3 mmol, 96%), m.p. 136-138° C., ESMS: $ES^+$, m/z 407 (M+1, base).

EXAMPLE 4

This Example illustrates the Preparation of D-4, which was prepared according to the following reaction scheme:

room temperature for 5 days. The solvents were distilled off, the residue was twice dissolved in toluene which was distilled off. The yield of 14 was 9.34 g (40.6 mmol, 100%).

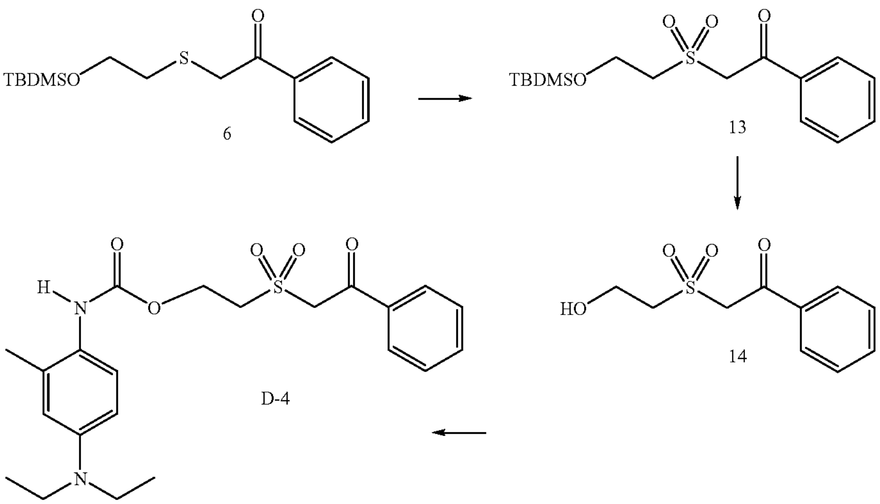

6, 13, 14, D-4

Preparation Of Intermediate 13:

A solution of m-chloroperbenzoic acid (77%, 51.47 g, 230 mmol) in 40 mL of dichloromethane was added over a period of 45 min to a solution of 6 (23.80 g, 76.7 mmol) in 150 mL of dichloromethane that was stirred at 5° C. The reaction was run for 18 h at room temperature and quenched with saturated aqueous sodium bicarbonate (350 mL) and the organic layer was dried and concentrated. Purification by column chromatography (silica, dichloromethane/heptane) gave 13.92 g of solid 13 (40.6 mmol, 53%).

Preparation Of Intermediate 14:

A solution of 13 (13.92 g, 40.6 mmol) in tetrahydrofuran (120 mL)/acetic acid (60 mL)/water (120 mL) was stirred at Preparation Of D-4:

A solution of 14 (9.34 g, 40.6 mmol), compound 3 (8.29 g, 40.6 mmol), and dibutyltin diacetate (0.03 mL) in acetonitrile (35 mL) was kept at room temperature in a stoppered flask for 3 days. The solvent was removed and the crude product purified by column chromatography (silica, ethyl acetate/heptane). Recrystallization from ethanol produced 5.85 g of D-4 (13.5 mmol, 33%), m.p. 102-103° C., ESMS: $ES^+$, m/433 (M+1, base).

EXAMPLE 5

This Example illustrates the Preparation of D-12, which was prepared according to the following reaction scheme:

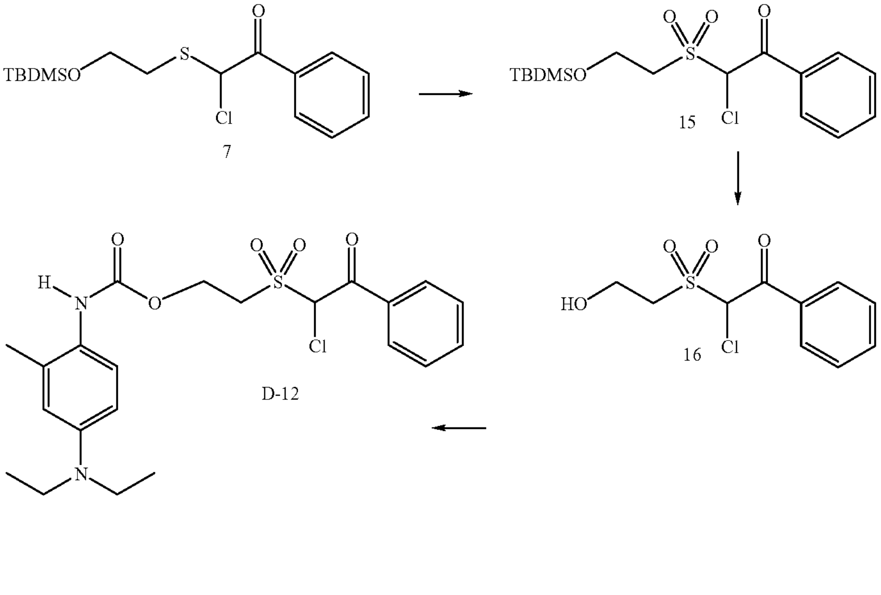

7, 15, 16, D-12

Preparation Of Intermediate 15:

Solid m-chloroperbenzoic acid (77%, 2.36 g, 10.5 mmol) was added in portions to a cold (−15° C.) solution of compound 7 (1.64 g, 4.75 mmol) in 30 mL of dichloromethane. The mixture was stirred at room temperature for 4 h and quenched with saturated aqueous sodium bicarbonate (20 mL) and the organic layer was dried and concentrated. Purification by column chromatography (silica, dichloromethane/heptane) gave 1.42 g of solid 15 (3.8 mmol, 79%).

Recrystallization from isopropyl ether produced 1.07 g of D-12 (2.3 mmol, 76%), m.p. 81-82° C., ESMS: $ES^+$, m/467 (M+1, base).

EXAMPLE 6

This Example illustrates the Preparation of D-3, which was prepared according to the following reaction scheme:

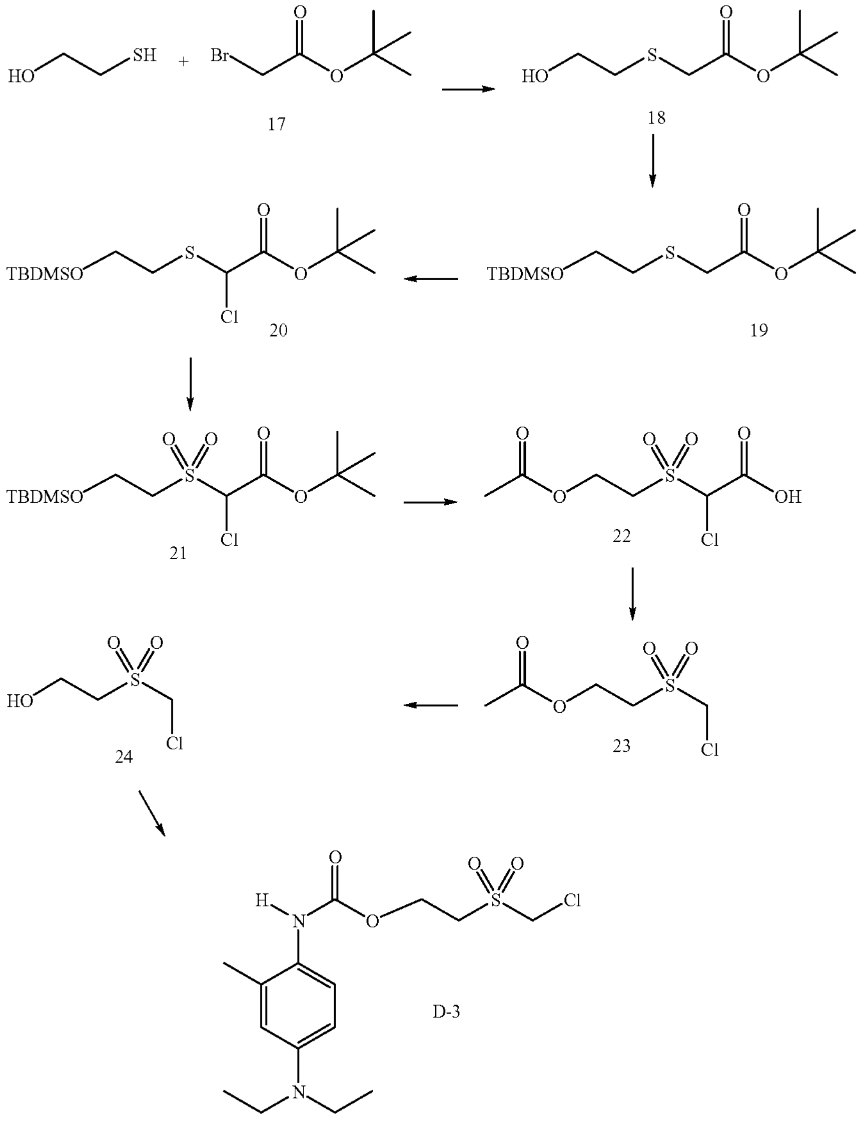

Preparation Of Intermediate 16:

A solution of 15 (1.36 g, 3.6 mmol) in tetrahydrofuran (10 mL)/acetic acid (30 mL)/water (10 mL) was stirred at room temperature for 3 days. The solvents were distilled off, the residue was twice dissolved in toluene which was distilled off giving a solid. The product was washed with isopropyl ether and dried. The yield of 16 was 0.83 g (3.2 mmol, 88%).

Preparation Of D-12:

A solution of 16 (0.61 g, 3 mmol), compound 3 (0.79 g, 3 mmol) and dibutyltin diacetate (0.01 mL) in acetonitrile (20 mL) was kept at room temperature in a stoppered flask for 3 days. The solvent was removed and the crude product purified by column chromatography (silica, ethyl acetate/heptane).

Preparation Of Intermediate 18:

A solution of t-butyl bromoacetate 17 (Aldrich, 19.51 g, 100 mmol) in 100 mL of acetonitrile was added in drops over a period of 30 min to a cooled (5° C.) solution of 2-mercaptoethanol (8.19 g, 105 mmol) in 100 mL of acetonitrile, containing potassium carbonate (15.20 g, 110 mmol). Following the addition the mixture was stirred at room temperature for 3 h and filtered. The filtrate was diluted with 200 mL of ether and washed with brine (50 mL). The ethereal solution was dried over sodium sulfate and concentrated in vacuo to give 19.24 g of 18 (100 mmol, 100%).

Preparation Of Intermediate 19:

Solid tert-butyldimethylsilyl chloride (TBDMSC1, 18.09 g, 120 mmol) was added in one portion to a solution of 18 (19.24 g, 100 mmol) and imidazole (9.55 g, 140 mmol) in 250 mL of tetrahydrofuran, stirred under nitrogen. After 2 h at room temperature the mixture was quenched with 200 mL of saturated aqueous sodium bicarbonate and extracted with ether. The crude product was filtered through silica gel (ether/heptane) giving 29.21 g (95 mmol, 95%) of 19.

Preparation Of Intermediate 20:

Solid N-chlorosuccinimide (6.68 g, 50 mmol) was added in portions over a period of 30 min to a solution of 19 (15.33 g, 50 mmol) in 100 mL of carbon tetrachloride that was stirred at 5° C. The reaction was run for 2 h and filtered. Removal of the solvent left 17.44 g of 20 as an oil (50 mmol, 100%).

Preparation Of Intermediate 21:

A solution of m-chloroperbenzoic acid (m-CPBA, 77%, 24.75 g, 110 mmol) in 200 mL of dichloromethane was added in drops over a period of 30 min to a solution of 20 (17.44 g, 50 mmol) in 100 mL of dichloromethane, stirred at 5° C. Following the addition, the mixture was stirred at 5° C. for 2 h and then at room temperature for 1 h. The reaction was quenched with saturated aqueous sodium bicarbonate (250 mL) and the organic layer was dried and concentrated giving 18.66 g of 21 as an oil (50 mmol, 100%).

Preparation Of Intermediate 22:

A solution of 21 (11.26 g, 30.2 mmol, ), acetic anhydride (5 mL) and p-toluenesulfonic acid monohydrate (100 mg) in acetic acid (150 mL) was refluxed for 1 h. The solution was cooled to room temperature, diluted with 100 mL of water and stirred for 2 h. A solid was filtered off and the filtrate was concentrated in vacuo to produce 22 as a colorless oil.

Preparation Of Intermediate 23:

A solution of crude 22 and sodium acetate (2.46 g, 30 mmol) in acetic acid (30 mL) was refluxed for 15 min, cooled to room temperature and the solvent was distilled off. The residue was worked up with water and ethyl acetate, giving 5.66 g of 23 as an oil.

Preparation Of Intermediate 24:

A solution of crude 23 and concentrated hydrochloric acid (0.5 mL) in 75 mL of methanol was stirred at room temperature for 3 days. The solvent was distilled off leaving 4.61 g of 24 (29 mmol, 96% based on 21).

Preparation Of D-3:

A solution of 24 (1.59 g, 10 mmol), 3 (2.25 g, 11 mmol) and dibutyltin diacetate (0.02 mL) in acetonitrile (10 mL) was kept at room temperature in a stoppered flask for 24 h. The solvent was removed giving an oil which crystallized when stirred with isopropyl ether. The solid was collected, washed with isopropyl ether and dried. The yield of D-3 was 3.03 g (8.3 mmol, 83%), m.p. 96-98° C., ESMS: $ES^+$, m/z 363 (M+1, 95%).

EXAMPLE 7

This Example illustrates the performance of a compound according to the present invention in a photographic element. The processing conditions are as described below with respect to each sample. Unless otherwise stated, the silver halide was removed after development by immersion in Kodak Flexicolor Fix solution. In general, an increase of approximately 0.2 in the measured density would be obtained by omission of this step. The following components are used in the samples, including is a list of all of the chemical structures.

Silver Salt Dispersion SS-1:

A stirred reaction vessel was charged with 431 g of lime processed gelatin and 6569 g of distilled water. A solution containing 214 g of benzotriazole, 2150 g of distilled water, and 790 g of 2.5 molar sodium hydroxide was prepared (Solution B). The mixture in the reaction vessel was adjusted to a pAg of 7.25 and a pH of 8.00 by additions of Solution B, nitric acid, and sodium hydroxide as needed.

A 4 1 solution of 0.54 molar silver nitrate was added to the kettle at 250 cc/minute, and the pAg was maintained at 7.25 by a simultaneous addition of solution B. This process was continued until the silver nitrate solution was exhausted, at which point the mixture was concentrated by ultrafiltration. The resulting silver salt dispersion contained fine particles of silver benzotriazole.

Emulsion E-1:

A silver halide tabular emulsion with a composition of 97% silver bromide and 3% silver iodide was prepared by conventional means. The resulting emulsion had an equivalent circular diameter of 0.6 microns and a thickness of 0.09 microns. This emulsion was spectrally sensitized to blue light by addition of dye SY-1 dye and then chemically sensitized for optimum performance.

Coupler Dispersion CDM-1:

An oil based coupler dispersion was prepared by conventional means containing coupler M-1 [224EV] with sensitizing dye SY-1 and tricresyl phosphate at a weight ratio of 1:0.5.

| EX. | Structure |
| --- | --- |
| DC-1 D94BM | 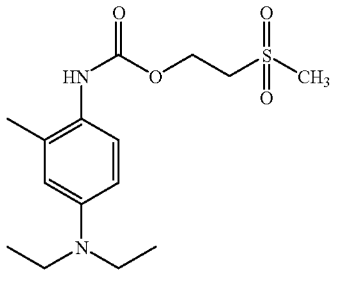 |

-continued

| EX. | Structure |
|---|---|
| DC-2 D94EJ | 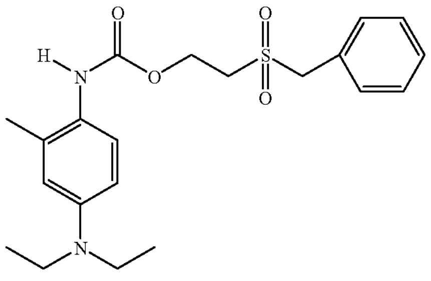 |
| M-1 | 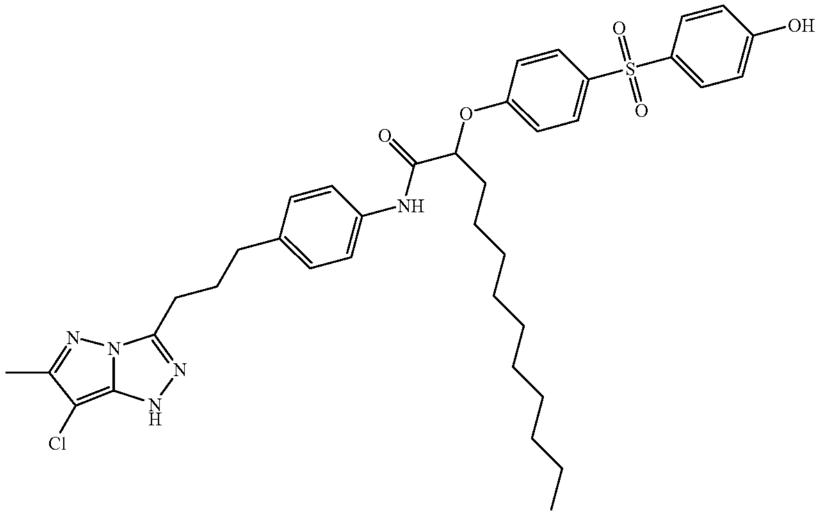 |
| SY-1 | 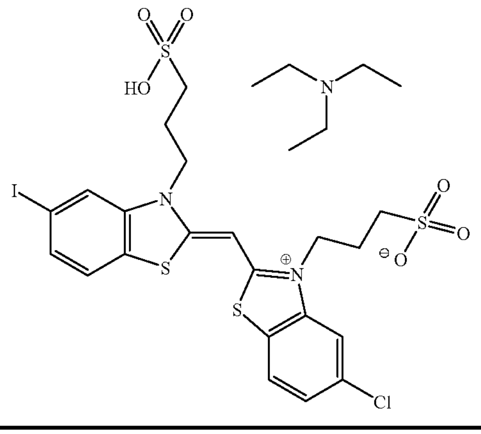 |

All coatings in this example were prepared according to the standard format listed in Table 1 below, with variations consisting of changing the incorporated developer. All coatings were prepared on a 7 mil thick poly(ethylene terephthalate) support.

Developers were ball-milled in an aqueous slurry for 3 days using Zirconia beads in the following formula. For each gram of incorporated developer, 0.2 g of sodium tri-isopropylnaphthalene sulfonate, 10 g of water, and 25 ml of beads were added. Following milling, the zirconia beads were removed by filtration. The slurry was refrigerated prior to use.

TABLE 1

| Component | Laydown |
|---|---|
| Silver (from emulsion E-1) | 0.54 $g/m^2$ |
| Silver (from silver salt SS-1) | 0.54 $g/m^2$ |
| Coupler M-1 (from coupler dispersion CDM-1) | 0.54 $g/m^2$ |
| Developer | 1.03 $mmol/m^2$ |
| Salicylanilide | 0.86 $g/m^2$ |
| 1-phenyl-5-mercapto tetrazole | 0.32 $g/m^2$ |
| Lime processed gelatin | 4.31 $g/m^2$ |

The resulting coatings were exposed through a step wedge to a 3.04 log lux light source at 3000K filtered by Daylight 5A and Wratten 2B filters. The exposure time was 1 second. After exposure, the coating was thermally processed by contact with a heated platen for 20 seconds. A number of strips were processed at a variety of platen temperatures in order to yield an optimum strip process condition. From this data, the onset temperature, $T_o$, was obtained. $T_o$ corresponds the temperature required to produce a maximum density (Dmax) of 0.5. Lower temperatures indicate more active developers which are desirable.

The coatings listed above performed as shown in Table 2 below.

TABLE 2

| Coating | Developer | $T_o$ (° C.) |
|---|---|---|
| C-1-1 (comparative) | DC-1 | 167 |
| C-1-2 (comparative) | DC-2 | 167 |
| I-1-1 (inventive) | D-7 | 145 |
| I-1-2 (inventive) | D-8 | 153 |

It can be seen from the results in Table 2 that the inventive developers offer reduced onset temperature which is a desirable in a blocked developer, other properties being equal.

EXAMPLE 8

All coatings in this example were prepared according to the standard format listed in Table 3 below, with variations consisting of changing the incorporated developer. All coatings were prepared on a 7 mil thick poly(ethylene terephthalate) support. The developers were milled and incorporated as described in Example 7.

TABLE 3

| Component | Laydown |
|---|---|
| Silver (from emulsion E-1) | 0.54 $g/m^2$ |
| Silver (from silver salt SS-1) | 0.54 $g/m^2$ |
| Coupler M-1 (from coupler dispersion CDM-1) | 0.54 $g/m^2$ |
| Base Releaser (Guanidine trichloroacetate) | 0.81 $g/m^2$ |
| Developer | 1.03 $mmol/m^2$ |
| Salicylanilide | 0.86 $g/m^2$ |
| 1-phenyl-5-mercapto tetrazole | 0.32 $g/m^2$ |
| Lime processed gelatin | 4.31 $g/m^2$ |

The resulting coatings were exposed through a step wedge to a 3.04 log lux light source at 3000K filtered by Daylight 5A and Wratten 2B filters. The exposure time was 1 second. After exposure, the coating was thermally processed by contact with a heated platen for 20 seconds. A number of strips were processed at a variety of platen temperatures in order to yield an optimum strip process condition. From this data, the parameters $T_o$ as described in example 1 was obtained. The performance of coatings in this example are shown in table 4.

TABLE 4

| Coating | Developer | $T_o$ (° C.) |
|---|---|---|
| C-2-1 (comparative) | DC-1 | 142 |
| C-2-2 (comparative) | DC-2 | 141 |
| I-2-1 (inventive) | D-7 | 136 |
| I-2-2 (inventive) | D-8 | 128 |

As can be seen from Table 4, the developers of this invention offer reduced onset temperature relative to comparative developers, which is a desirable feature for a blocked developer.

EXAMPLE 9

This Example illustrates solution reactivity measurements. To obtain the solution reactivity of a blocked compound, an aqueous alcohol solution was used which was prepared with phosphate buffers and ethanol (33%) at ionic strength 0.125 and pH 7.87. A blocked developer compound, e.g., D-3 was dissolved in the solution at ~$1.6\times10^{-5}$ M, and heated at 60° C. in the presence of Coupler-1 (0.0004 M) and $K_3Fe(CN)_6$ (0.00036 M). The reaction is followed by measurement of the magenta dye formed at 568 nm in a 1-cm cell with a spectrophotometer, and the reaction rate constant (k) is obtained from a fit of the following equation to the data:

$$A = A_0 + A_\infty(1 - e^{-kt})$$

$$k'_{rel} = \ln\frac{A_\infty - A_0}{A - A_0}$$

Where A is the absorbance at 568 nm at time t, and the subscripts denote time 0 and infinity (∞).

Coupler-1

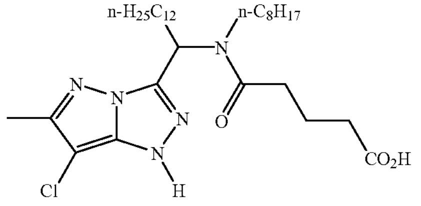

Table 5 shows the rate constants under the aforementioned conditions (aqueous alcohol solutions, 60° C.) for blocked developer compounds according to Structure I. As can be seen, the inventive blocked developers exhibit higher reactivity when electron-withdrawing groups ($\sigma_I$>0.2) are attached to the methylsulfone carbon.

TABLE 5

| D94 | Developer | W | $\sigma_I$ | $Log^k$ | $t_{1/2}$, sec |
|---|---|---|---|---|---|
| BM | DC-1 (comparative) | H | 0.00 | −4.04 | 7598 |
| EJ | DC-2 (comparative) | Ph | 0.10 | −3.64 | 2992 |
| JS | D-4 (inventive) | PhCO | 0.29 | −2.85 | 490.8 |
| JU | D-6 (inventive) | $SO_2CH_3$ | 0.59 | −1.90 | 55.41 |
| JW | D-3 (inventive) | Cl | 0.43 | −2.23 | 117.0 |
| JB | D-7 (inventive) | CN | 0.63 | −1.50 | 22.10 |
| JQ | D-12 (inventive) | Cl, PhCO | 0.72 | −1.45 | 19.62 |
| JC | D-8 (inventive) | $CO_2Et$ | 0.31 | −2.83 | 467.7 |

The invention has been described in detail with particular reference to preferred embodiments, but it will be understood that variations and modifications can be effected within the spirit and scope of the invention.

What is claimed is:

1. A compound useful in an imaging element represented by the following structure:

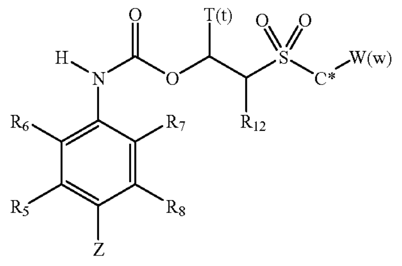

wherein:

w is 1 or 2;

t is 0, 1 or 2;

Z is OH or $NR_2R_3$, where $R_2$ and $R_3$ are independently hydrogen or a substituted or unsubstituted alkyl group or $R_2$ and $R_3$ are connected to form a ring;

$R_5$, $R_6$, $R_7$, and $R_8$ are independently hydrogen, halogen, hydroxy, amino, alkoxy, carbonamido, sulfonamido, alkylsulfonamido or alkyl, or $R_5$ can connect with $R_3$ or $R_6$ and/or $R_8$ can connect to $R_2$ or $R_7$ to form a ring;

T is a substituted or unsubstituted alkyl group, cycloalkyl group, aryl, or heterocyclic group, an inorganic monovalent electron withdrawing group, or an inorganic divalent electron withdrawing group capped with at least one organic group; or T is joined with W, C* or $R_{12}$ to form a ring; when T is an aryl group, it can also combine with W, C* or $R_{12}$ to form a ring;

$R_{12}$ is hydrogen, or a substituted or unsubstituted alkyl, cycloalkyl, aryl or heterocyclic group;

C* is a tetrahedral carbon; and

W is a monovalent electron withdrawing group, a divalent electron withdrawing group, an aryl group substituted with one to seven electron withdrawing groups, or a substituted or unsubstituted heteroaromatic group; when W is a divalent electron withdrawing group, an aryl group, or a heteroaromatic group, it can combine with C*, $R_{12}$, or T to form a ring; when w is 2, the two W groups can form a ring; and C* may be attached to one or two hydrogen atoms or to one hydrogen atom and one substituted or unsubstituted alkyl group that is not an electron withdrawing group or an aryl group that is not substituted with an electron-withdrawing group;

wherein a single blocked developing is present.

2. The compound of claim 1 wherein when W is a divalent electron withdrawing group, it is selected from the group consisting of $—SO_2R_{13}$, $—OSO_2R_{13}$, $—NR_{13}(SO_2R_{14})$, $—CO_2R_{13}$, $—COR_{13}$, $—NR_{13}(COR_{14})$, wherein $R_{13}$ and $R_{14}$ are independently substituted or unsubstituted alkyl, aryl, or heterocyclic group having 1 to 8 carbon atoms.

3. A compound useful in an imaging element represented by the following structure:

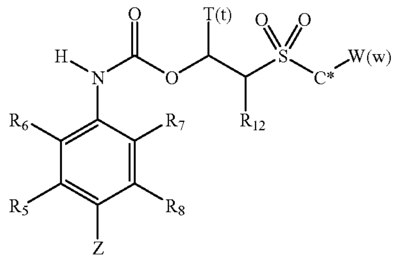

wherein:

w is 1 or 2;

t is 0, 1 or 2;

Z is OH or $NR_2R_3$, where $R_2$ and $R_3$ are independently hydrogen or a substituted or unsubstituted alkyl group or $R_2$ and $R_3$ are connected to form a ring;

$R_5$, $R_6$, $R_7$, and $R_8$ are independently hydrogen, halogen, hydroxy, amino, alkoxy, carbonamido, sulfonamido, alkylsulfonamido or alkyl, or $R_5$ can connect with $R_3$ or $R_6$ and/or $R_8$ can connect to $R_2$ or $R_7$ to form a ring;

T is a substituted or unsubstituted alkyl group, cycloalkyl group, aryl, or heterocyclic group, an inorganic monovalent electron withdrawing group, or an inorganic divalent electron withdrawing group capped with at least one organic group; or T is joined with W, C* or $R_{12}$ to form a ring; when T is an aryl group, it can also combine with W, C* or $R_{12}$ to form a ring;

$R_{12}$ is hydrogen, or a substituted or unsubstituted alkyl, cycloalkyl, aryl or heterocyclic group;

C* is a tetrahedral carbon; and

W is a monovalent electron withdrawing group, a divalent electron withdrawing group, an aryl group substituted with one to seven electron withdrawing groups, or a substituted or unsubstituted heteroaromatic group; when W is a divalent electron withdrawing group, an aryl group, or a heteroaromatic group, it can combine with C*, $R_{12}$, or T to form a ring; when w is 2, the two W groups can form a ring; and C* may be attached to one or two hydrogen atoms or to one hydrogen atom and one substituted or unsubstituted alkyl group that is not an electron withdrawing group or an aryl group that is not substituted with an electron-withdrawing group;

wherein when W is a divalent electron withdrawing group, it is selected from the group consisting of $—SO_2R_{13}$, $—OSO_2R_{13}$, $—NR_{13}(SO_2R_{14})$, $—CO_2R_{13}$, $—COR_{13}$, $—NR_{13}(COR_{14})$, wherein $R_{13}$ and $R_{14}$ are independently substituted or unsubstituted alkyl, aryl, or heterocyclic group having 1 to 8 carbon atoms.

4. A compound according to claim 3 wherein W is a monovalent electron withdrawing group selected from the group consisting of halogen, $—NO_2$, —CN, and a halogenated alkyl group.

5. A compound according to claim 3 wherein W is an aryl group or an aryl group substituted with one to seven electron withdrawing groups.

6. A compound according to claim 3 wherein W is a substituted or unsubstituted heteroaromatic group.

* * * * *